(12) United States Patent
Kaula et al.

(10) Patent No.: US 9,669,227 B2
(45) Date of Patent: Jun. 6, 2017

(54) SYSTEMS, METHODS, AND DEVICES FOR GENERATING ARBITRARY STIMULATION WAVEFORMS

(71) Applicant: Nuvectra Corporation, Plano, TX (US)

(72) Inventors: Norbert Kaula, Arvada, CO (US); Yohannes Iyassu, Denver, CO (US)

(73) Assignee: NUVECTRA CORPORATION, Plano, TX (US)

( * ) Notice: Subject to any disclaimer, the term of this patent is extended or adjusted under 35 U.S.C. 154(b) by 0 days.

(21) Appl. No.: 14/932,130

(22) Filed: Nov. 4, 2015

(65) Prior Publication Data
US 2016/0361551 A1 Dec. 15, 2016

Related U.S. Application Data

(60) Provisional application No. 61/181,827, filed on Jun. 19, 2015, provisional application No. 62/173,118, filed on Jun. 9, 2015.

(51) Int. Cl.
*A61N 1/00* (2006.01)
*A61N 1/372* (2006.01)
(Continued)

(52) U.S. Cl.
CPC ....... *A61N 1/37247* (2013.01); *A61N 1/3605* (2013.01); *A61N 1/37264* (2013.01); *G06F 19/3406* (2013.01)

(58) Field of Classification Search
CPC .............. A61N 1/37247; A61N 1/3605; A61N 1/37264; A61N 1/36146; G06F 19/3406
See application file for complete search history.

(56) References Cited

U.S. PATENT DOCUMENTS 4,245,641 A 1/1981 Mann et al.
4,503,863 A 3/1985 Katims
(Continued)

FOREIGN PATENT DOCUMENTS

EP 1 048 317 11/2000
EP 2 567 729 3/2013
(Continued)

OTHER PUBLICATIONS

EPO, European Search Report for EP16172698 dated Sep. 8, 2016.
(Continued)

*Primary Examiner* — Robert N Wieland
(74) *Attorney, Agent, or Firm* — Haynes and Boone, LLP; Eric Li

(57) ABSTRACT

Electrical stimulation therapy is provided for a patient. A user is informed that a user-supplied electrical stimulation waveform can be entered into an electronic programmer. At least in part via a user interface of the electronic programmer, it is detected that the user-supplied electrical stimulation waveform has been received by the electronic programmer. A determination is made as to whether the user-supplied electrical stimulation waveform is compliant with a set of predetermined restrictions. In response to a determination that the user-supplied electrical stimulation waveform is compliant with the set of predetermined restrictions, a pulse generator is instructed to generate electrical stimulation pulses based on the user-supplied electrical stimulation waveform.

20 Claims, 23 Drawing Sheets

(51) Int. Cl.
*G06F 19/00* (2011.01)
*A61N 1/36* (2006.01)

(56) References Cited

U.S. PATENT DOCUMENTS

| | | | |
|---|---|---|---|
| 5,725,560 | A | 3/1998 | Brink |
| 6,275,735 | B1 | 8/2001 | Jarding et al. |
| 6,505,074 | B2 | 1/2003 | Boveja et al. |
| 7,174,213 | B2 | 2/2007 | Pless |
| 7,601,116 | B2 | 10/2009 | Fischell et al. |
| 8,060,208 | B2 | 11/2011 | Kilgore et al. |
| 8,095,216 | B1 | 1/2012 | Moulder et al. |
| 8,112,154 | B2 | 2/2012 | Rezai et al. |
| 8,260,412 | B2 | 9/2012 | Krause et al. |
| 8,688,217 | B2 | 4/2014 | Aghassian et al. |
| 8,751,016 | B2 | 6/2014 | Schleicher et al. |
| 8,761,897 | B2 | 6/2014 | Kaula et al. |
| 8,805,515 | B2 | 8/2014 | York et al. |
| 9,014,813 | B2 | 4/2015 | Foutz et al. |
| 9,144,680 | B2 | 9/2015 | Kaula et al. |
| 2004/0098065 | A1 | 5/2004 | Hagglof et al. |
| 2006/0122660 | A1 | 6/2006 | Boveja et al. |
| 2010/0280575 | A1 | 11/2010 | Carbunaru et al. |
| 2011/0307032 | A1 | 12/2011 | Goetz et al. |
| 2012/0101326 | A1 | 4/2012 | Simon et al. |
| 2013/0296966 | A1 | 11/2013 | Wongsarnpigoon et al. |
| 2013/0304152 | A1 | 11/2013 | Bradley et al. |
| 2014/0046398 | A1 | 2/2014 | Sachs et al. |
| 2014/0067013 | A1 | 3/2014 | Kaula et al. |
| 2014/0067020 | A1 | 3/2014 | Kaula et al. |
| 2014/0068758 | A1 | 3/2014 | Kaula et al. |
| 2014/0180361 | A1 | 6/2014 | Burdick et al. |
| 2014/0222102 | A1 | 8/2014 | Lemus et al. |
| 2014/0249599 | A1 | 9/2014 | Kaula et al. |
| 2015/0134027 | A1 | 5/2015 | Kaula et al. |
| 2015/0134028 | A1 | 5/2015 | Kaula et al. |
| 2016/0022996 | A1 | 1/2016 | Kaula et al. |
| 2016/0121126 | A1* | 5/2016 | Marnfeldt .......... A61N 1/36167 607/59 |

FOREIGN PATENT DOCUMENTS

| | | |
|---|---|---|
| WO | WO 2006/107848 | 10/2006 |
| WO | WO 2009/097224 | 8/2009 |
| WO | WO 2011/156288 | 12/2011 |

OTHER PUBLICATIONS

EPO, European Search Report for EP16172706 dated Oct. 10, 2016.
European Patent Office, "European Search Report" for Application No. 16172702.9, mailed Oct. 26, 2016, 8 pages.
European Patent Office, "European Search Report" for Application No. 16173541.0, mailed Nov. 3, 2016, 6 pages.

* cited by examiner ically coupled to the pulse generator through a communications link, wherein the electronic device is configured to perform the following steps: informing a user that a user-supplied electrical stimulation waveform can be entered into the electronic programmer; detecting, at least in part via the user interface of the electronic programmer, that the user-supplied electrical stimulation waveform has been received by the electronic programmer; determining whether the user-supplied electrical stimulation waveform is compliant with a set of predetermined restrictions; and instructing, in response to a determination that the user-supplied electrical stimulation waveform is compliant with the set of predetermined restrictions, a pulse generator to generate electrical stimulation pulses based on the user-supplied electrical stimulation waveform.

SYSTEMS, METHODS, AND DEVICES FOR GENERATING ARBITRARY STIMULATION WAVEFORMS

PRIORITY DATA

The present application is a utility application of provisional U.S. Patent Application No. 62/173,118, filed on Jun. 9, 2015, entitled "ADVANCED METHODS AND APPARATUSES FOR PERFORMING PELVIC NERVE STIMULATION," and a utility application of provisional U.S. Patent Application No. 62/181,827, filed on Jun. 19, 2015, entitled "ADVANCED METHODS AND APPARATUSES FOR PERFORMING PELVIC NERVE STIMULATION," the disclosures of each which are hereby incorporated by reference in their respective entireties.

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients or restore bodily functions.

Implantable medical devices (for example a neuro stimulator) can be controlled using an electronic programming device such as a clinician programmer or a patient programmer. These programmers can be used by medical personnel or the patient to define the particular electrical stimulation therapy to be delivered to a target area of the patient's body, alter one or more parameters of the electrical stimulation therapy, or otherwise conduct communications with a patient. Advances in the medical device field have improved these electronic programmers in certain aspects involving speed and user-friendliness. However, existing electronic programmers still have a variety of shortcomings. For example, when users perform the stimulation programming using existing programmers, only a few predefined waveforms are available to be used as the stimulation pulses. The dearth of available stimulation waveforms restrict the flexibility and versatility of stimulation programming.

Therefore, although existing electronic programmers for controlling implantable medical devices have been generally adequate for their intended purposes, they have not been entirely satisfactory in every aspect.

SUMMARY

One aspect of the present disclosure involves an electronic device for programming electrical stimulation therapy for a patient. The electronic device includes a user interface configured to receive an input from a user and communicate an output to the user; an electronic memory storage configured to store programming instructions; and one or more processors configured to execute the programming instructions to perform the following steps: informing a user that a user-supplied electrical stimulation waveform can be entered into the electronic programmer; detecting, at least in part via the user interface of the electronic programmer, that the user-supplied electrical stimulation waveform has been received by the electronic programmer; determining whether the user-supplied electrical stimulation waveform is compliant with a set of predetermined restrictions; and instructing, in response to a determination that the user-supplied electrical stimulation waveform is compliant with the set of predetermined restrictions, a pulse generator to generate electrical stimulation pulses based on the user-supplied electrical stimulation waveform.

Another aspect of the present disclosure involves a medical system. The medical system includes: a pulse generator configured to generate electrical stimulation pulses as a part of an electrical stimulation therapy for a patient; an electronic programmer that is telecommunicatively coupled to the pulse generator through a communications link, wherein the electronic device is configured to perform the following steps: informing a user that a user-supplied electrical stimulation waveform can be entered into the electronic programmer; detecting, at least in part via the user interface of the electronic programmer, that the user-supplied electrical stimulation waveform has been received by the electronic programmer; determining whether the user-supplied electrical stimulation waveform is compliant with a set of predetermined restrictions; and instructing, in response to a determination that the user-supplied electrical stimulation waveform is compliant with the set of predetermined restrictions, the pulse generator to generate electrical stimulation pulses based on the user-supplied electrical stimulation waveform.

Yet another aspect of the present disclosure involves a method of providing electrical stimulation therapy for a patient. The method includes the following steps: informing a user that a a user-supplied electrical stimulation waveform can be entered into an electronic programmer; detecting, at least in part via a user interface of the electronic programmer, that the user-supplied electrical stimulation waveform has been received by the electronic programmer; determining whether the user-supplied electrical stimulation waveform is compliant with a set of predetermined restrictions; and instructing, in response to a determination that the user-supplied electrical stimulation waveform is compliant with the set of predetermined restrictions, a pulse generator to generate electrical stimulation pulses based on the user-supplied electrical stimulation waveform.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
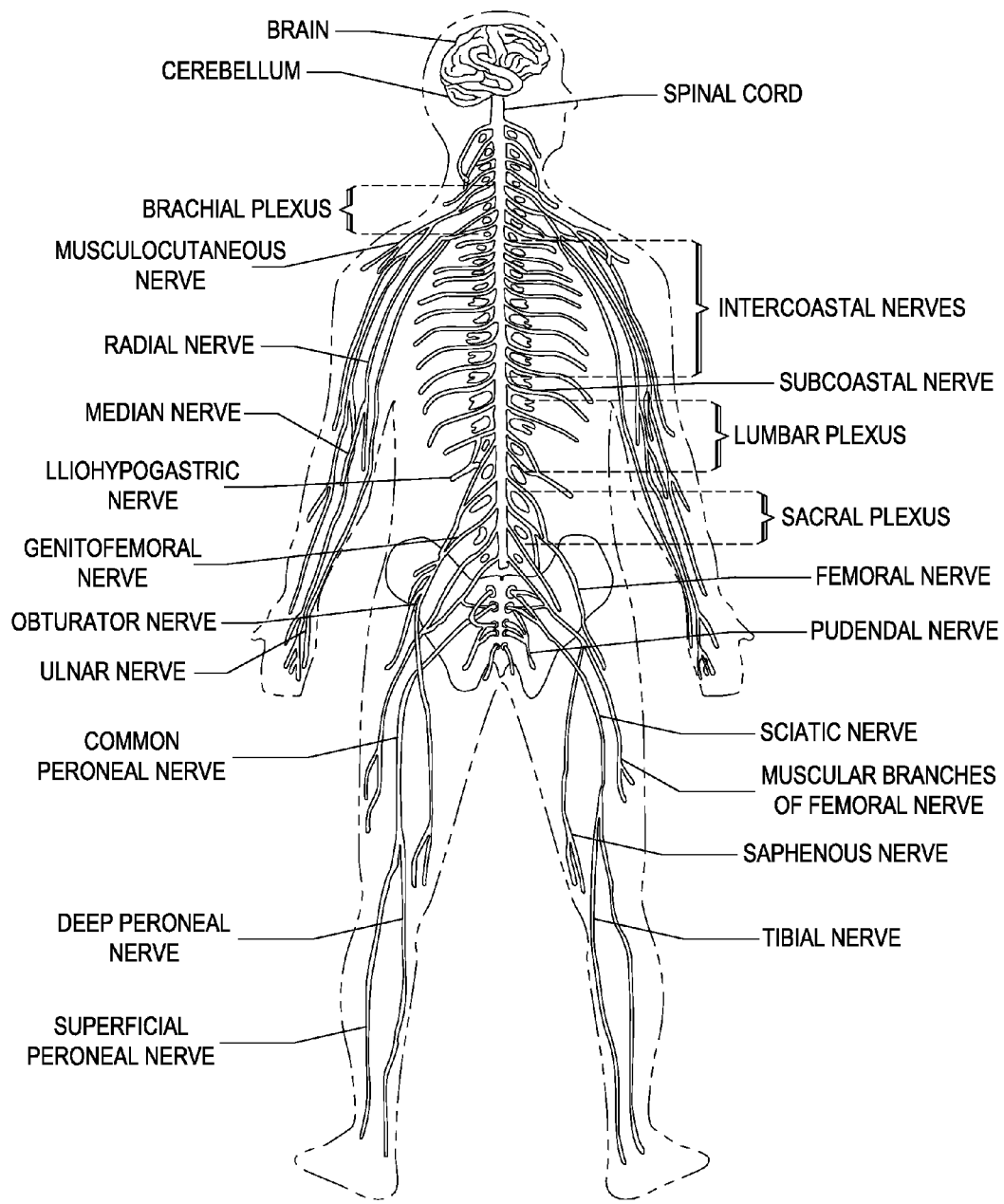
FIG. 1 is stylized overview of the human nervous system.

The human nervous system includes a complex network of neurological structures that extend throughout the body. As shown in FIG. 1, the brain interconnects with the spinal cord which branches into the brachial plexus near the shoulders and the lumbar plexus and sacral plexus in the lower back. The limb peripheral nerves of the arms extend distally from the brachial plexus down each arm. Similarly, the limb peripheral nerves of the legs extend distally from the lumbar plexus and sacral plexus. A number of the larger limb peripheral nerves are identified in FIG. 1. As discussed further below, certain aspects of the present invention are suited to stimulation of the nerves shown in FIG. 1, including the spinal cord, the pudendal nerves, and the sacral nerves, etc.

Figure 2B:
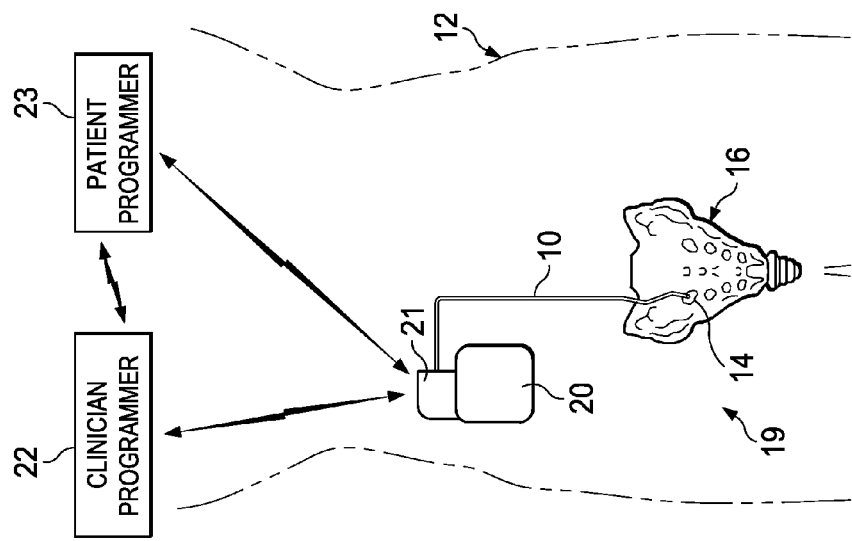
FIG. 2B is a simplified diagram illustrating an implantable neurostimulation system for stimulating nerves according to various embodiments of the present disclosure.
Figure 2A:
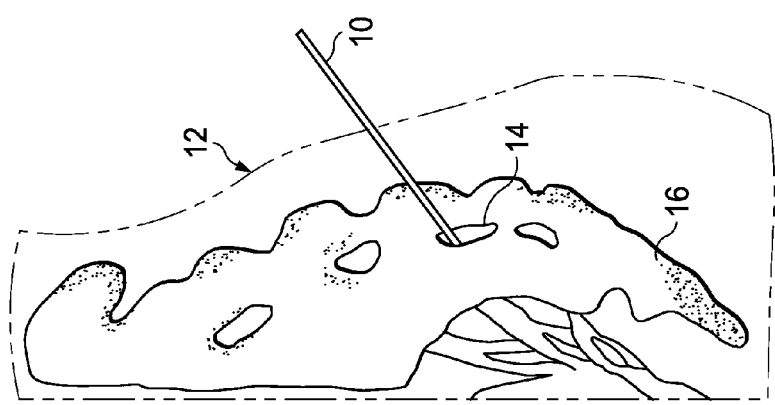
FIG. 2A is a diagram illustrating an example sacral implantation of a neurostimulation lead according to various embodiments of the present disclosure.

FIG. 2A is a simplified diagram illustrating implantation of a neurostimulation lead 10 according to some embodiments of the present disclosure. In the example of FIG. 2A, lead 10 is inserted into body 12 of a patient, and implanted posterior to one of dorsal foramen 14 of sacrum 16. However, lead 10 alternatively may be positioned to stimulate pudendal nerves, perineal nerves, sacral spinal nerves, or other areas of the nervous system. Lead 10 may be implanted via a needle and stylet for minimal invasiveness. Positioning of lead 10 may be aided by imaging techniques, such as fluoroscopy. In some embodiments, a plurality of stimulation leads may be provided.

FIG. 2B is a diagram illustrating an implantable neurostimulation system 19 for stimulating a nerve, such as a sacral nerve, via the lead 10. Neurostimulation system 19 delivers neurostimulation to the sacral nerves or other regions of the nervous system known to treat problems including, but are not limited to: pelvic floor disorders, urinary control disorders, fecal control disorders, interstitial cystitis, sexual dysfunction, and pelvic pain. As shown in FIG. 2B, system 19 includes lead 10 and an implantable pulse generator (IPG). In addition, a proximal end of stimulation lead 10 may be coupled to a connector block 21 associated with the neurostimulator 20.

In some embodiments, the neurostimulator 20 includes an implantable pulse generator (IPG), and delivers neurostimulation therapy to patient 12 in the form of electrical pulses generated by the IPG. In the example of FIG. 2B, the neurostimulator 20 is implanted in the upper left buttock of patient 12, but it is understood that the neurostimulator 20 be implanted at other locations in alternative embodiments.

The lead 10 carries one or more of stimulation electrodes, e.g., 1 to 8 electrodes, to permit delivery of electrical stimulation to the target nerve, such as the sacral nerve. For example, the implantable neurostimulation system 19 may stimulate organs involved in urinary, fecal or sexual function via C-fibers or sacral nerves at the second, third, and fourth sacral nerve positions, commonly referred to as S2, S3, and S4, respectively. In some embodiments, the neurostimulator 20 may be coupled to two or more leads deployed at different positions, e.g., relative to the spinal cord or sacral nerves.

The implantable neurostimulation system 19 also may include a clinician programmer 22 and a patient programmer 23. The clinician programmer 22 may be a handheld computing device that permits a clinician to program neurostimulation therapy for patient 12, e.g., using input keys and a display. For example, using clinician programmer 22, the clinician may specify neurostimulation parameters for use in delivery of neurostimulation therapy. The clinician programmer 22 supports radio frequency telemetry with neurostimulator 20 to download neurostimulation parameters and, optionally, upload operational or physiological data stored by the neurostimulator. In this manner, the clinician may periodically interrogate neurostimulator 20 to evaluate efficacy and, if necessary, modifies the stimulation parameters.

Similar to clinician programmer 22, patient programmer 23 may be a handheld computing device. The patient programmer 23 may also include a display and input keys to allow patient 12 to interact with patient programmer 23 and implantable neuro stimulator 20. In this manner, the patient programmer 23 provides the patient 12 with an interface for control of neurostimulation therapy by neurostimulator 20. For example, the patient 12 may use patient programmer 23 to start, stop or adjust neurostimulation therapy. In particular, the patient programmer 23 may permit the patient 12 to adjust stimulation parameters such as duration, amplitude, pulse width and pulse rate, within an adjustment range specified by the clinician via the clinician programmer 22.

The neurostimulator 20, clinician programmer 22, and patient programmer 23 may communicate via wireless communication, as shown in FIG. 2B. The clinician programmer 22 and patient programmer 23 may, for example, communicate via wireless communication with neurostimulator 20 using RF telemetry techniques known in the art. The clinician programmer 22 and patient programmer 23 also may communicate with each other using any of a variety of local wireless communication techniques, such as RF communication according to the 802.11 or Bluetooth specification sets, or other standard or proprietary telemetry protocols. It is also understood that although FIG. 2B illustrates the patient programmer 22 and the clinician programmer 23 as two separate devices, they may be integrated into a single programmer in some embodiments.

Figure 2C:
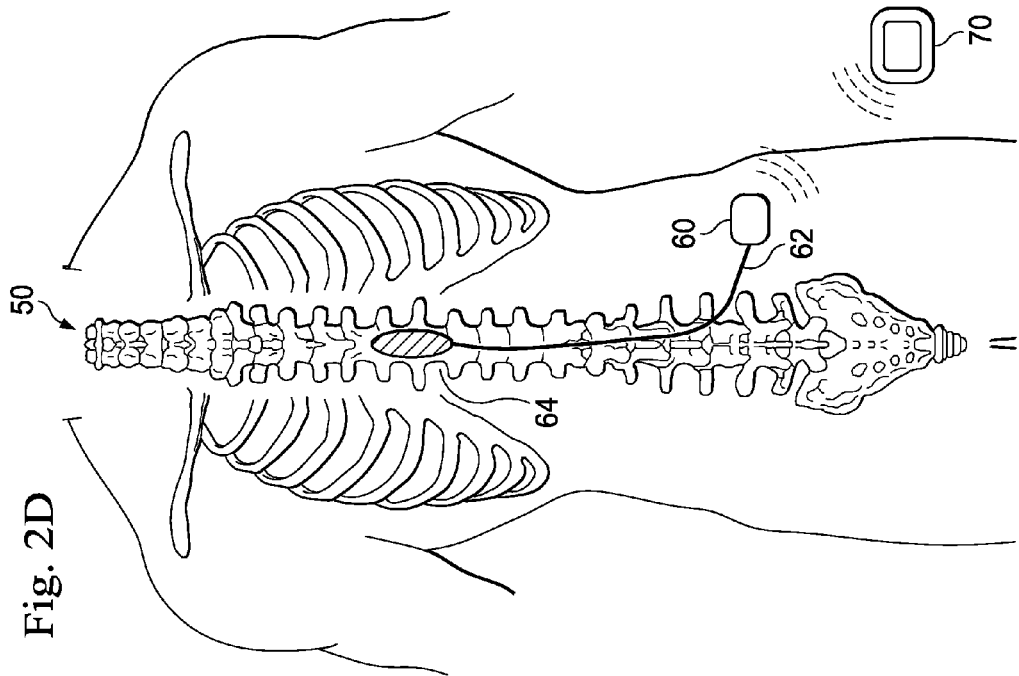
FIG. 2C includes a side view of a spine 50 according to various embodiments of the present disclosure.
Figure 2D:
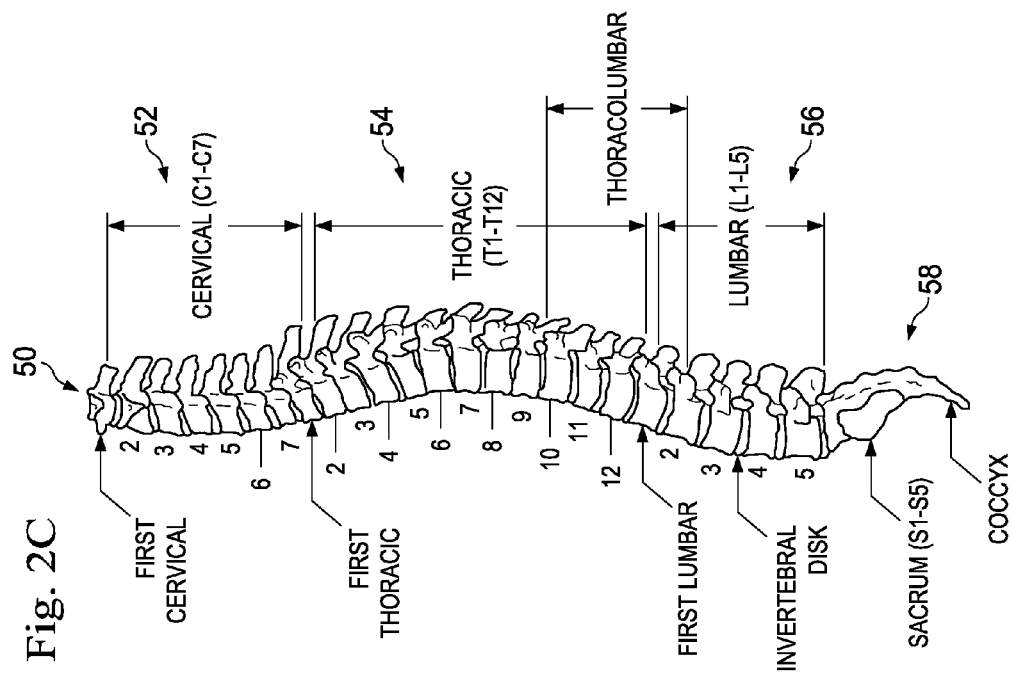
FIG. 2D includes a posterior view of the spine 50 according to various embodiments of the present disclosure.

The present disclosure also applies to other types of neuromodulation, for example deep brain stimulation (DBS), peripheral nerve stimulation (PNS), or spinal cord stimulation (SCS). An example SCS system is illustrated with reference to FIGS. 2C and 2D. Specifically, FIG. 2C includes a side view of a spine 50, and FIG. 2D includes a posterior view of the spine 50. The spine 50 includes a cervical region 52, a thoracic region 54, a lumbar region 56, and a sacrococcygeal region 58. The cervical region 52 includes the top 7 vertebrae, which may be designated with C1-C7. The thoracic region 54 includes the next 12 vertebrae below the cervical region 52, which may be designated with T1-T12. The lumbar region 56 includes the final 5 "true" vertebrae, which may be designated with L1-L5. The sacrococcygeal region 58 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 2D, an IPG device 60 (similar to the neurostimulator 20 in FIG. 2B) is implanted inside the body. A conductive lead 62 is electrically coupled to the circuitry inside the IPG device 60. The conductive lead 62 may be removably coupled to the IPG device 60 through a connector. A distal end of the conductive lead 62 is attached to one or more electrodes 64. The electrodes 64 are implanted adjacent to a desired nerve tissue in the thoracic region 54. Using well-established and known techniques in the art, the distal end of the lead 62 with its accompanying electrodes may be positioned along or near the epidural space of the spinal cord. It is understood that although only one conductive lead 62 is shown herein for the sake of simplicity, more than one conductive lead 62 and corresponding electrodes 64 may be implanted and connected to the IPG device 60.

The electrodes 64 deliver current drawn from the current sources in the IPG device 60, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 60, the lead 62, and the electrodes 64 may be implanted completely inside the body, may be positioned completely outside the body or may have only one or more components implanted within the body while other components remain outside the body. When they are implanted inside the body, the implant location may be adjusted (e.g., anywhere along the spine 50) to deliver the intended therapeutic effects of spinal cord electrical stimulation in a desired region of the spine. Furthermore, it is understood that the IPG device 60 may be controlled by an electronic programmer, for example the clinician programmer 22 or the patient programmer 23 shown in FIG. 2B.

Figure 3A:
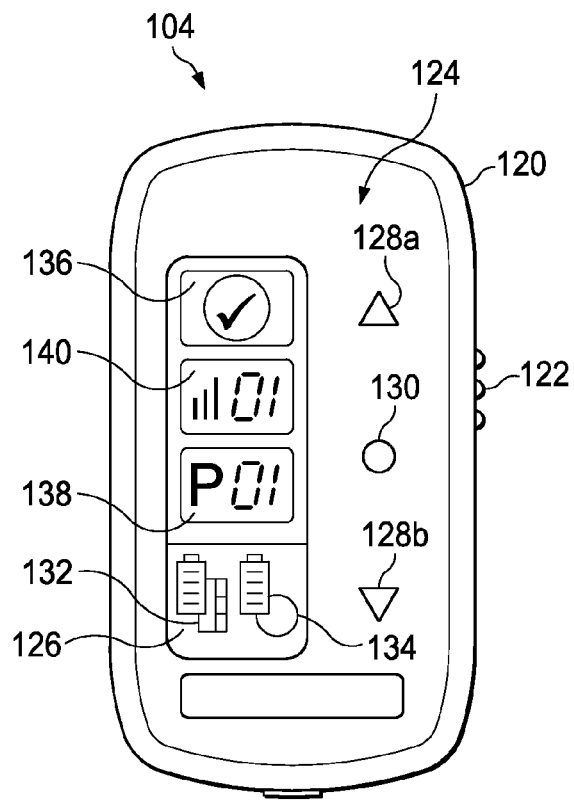
FIGS. 3A-3B illustrate an example pocket programmer controller in accordance with one embodiment of the present disclosure.
Figure 3B:
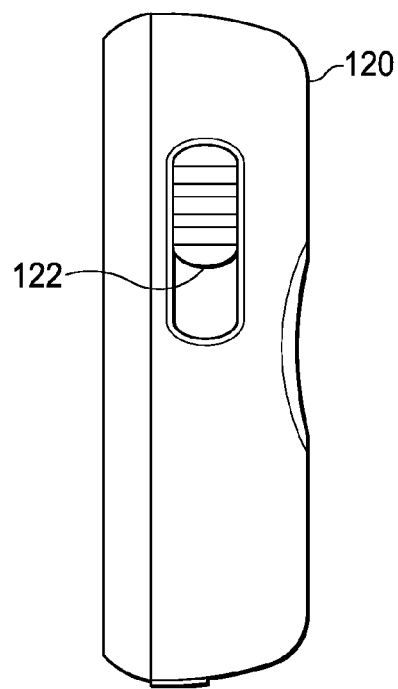
Figure 4:
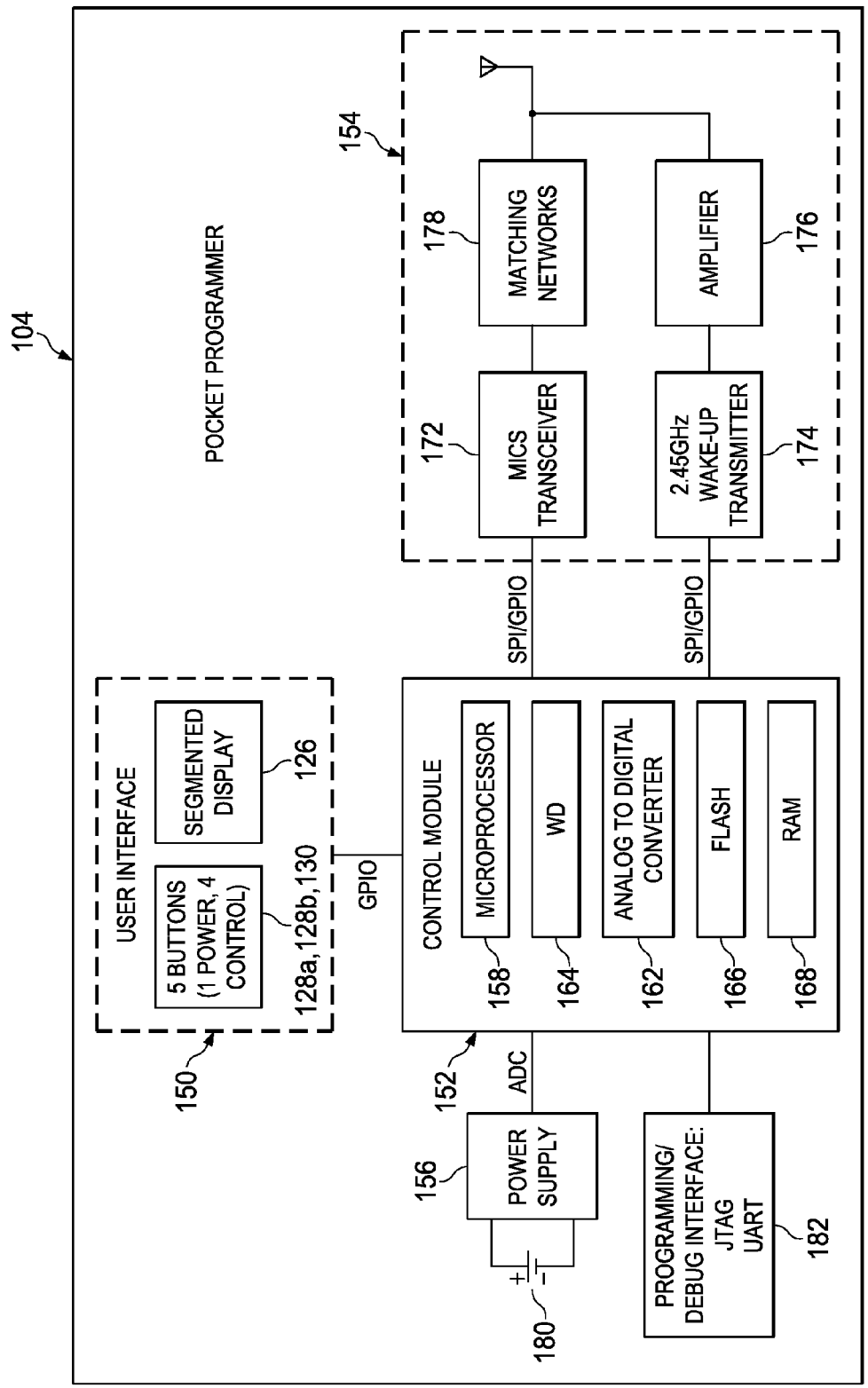
FIG. 4 is a block diagram of components of the example pocket controller of FIGS. 3A-3B in accordance with one embodiment of the present disclosure.
Figure 5A:
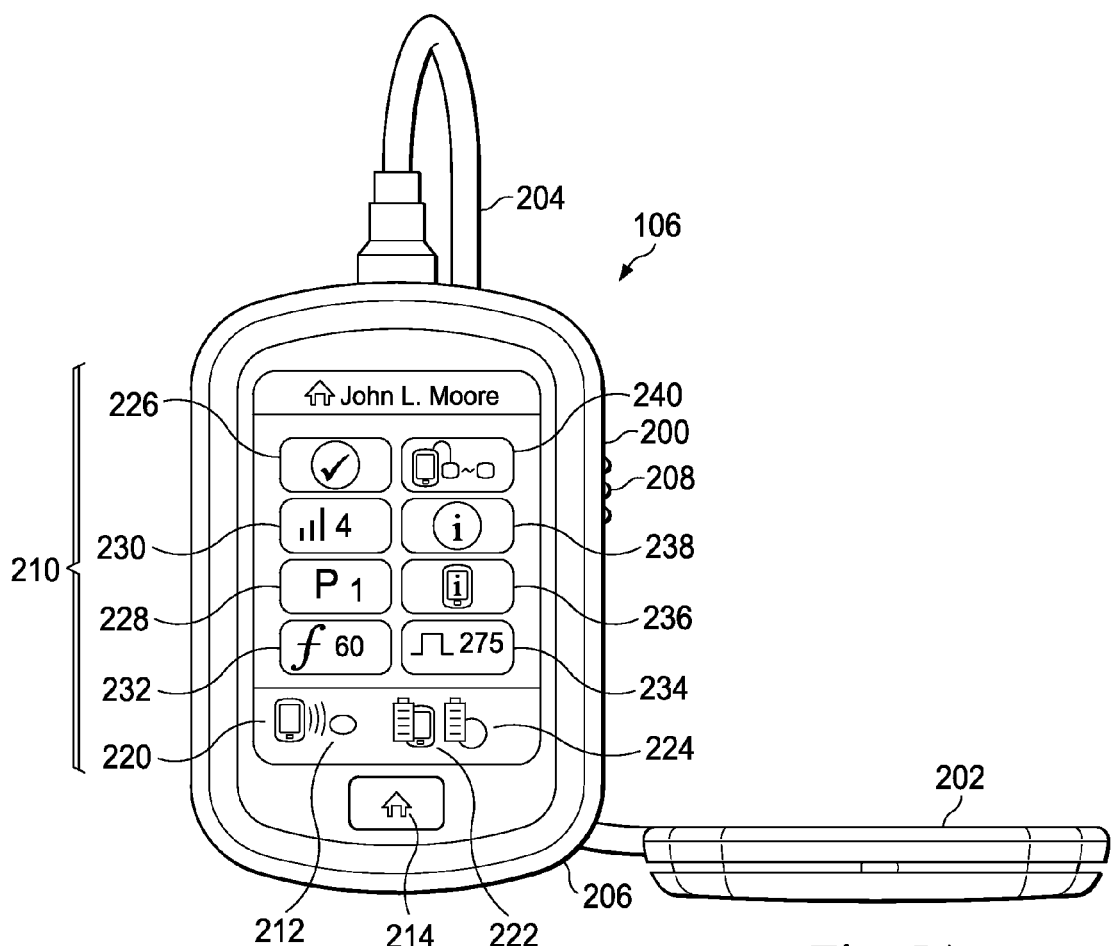
FIGS. 5A-5B illustrate an example patient programmer charger controller in accordance with one embodiment of the present disclosure.
Figure 5B:
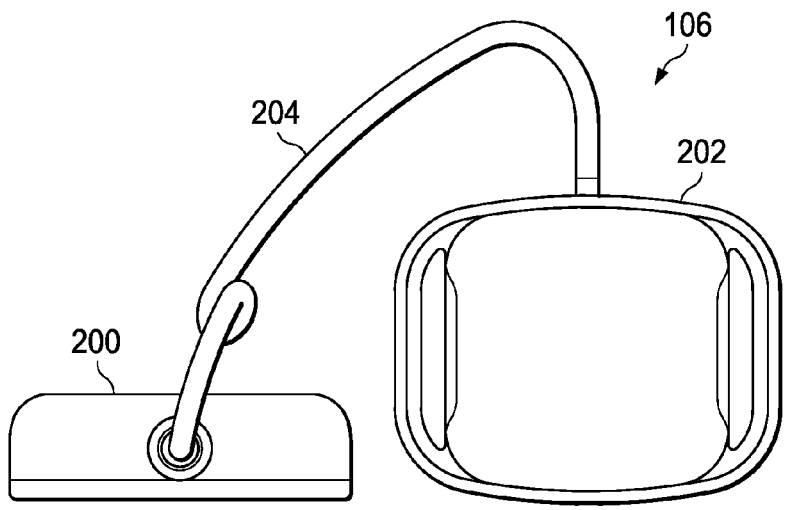
Figure 6:
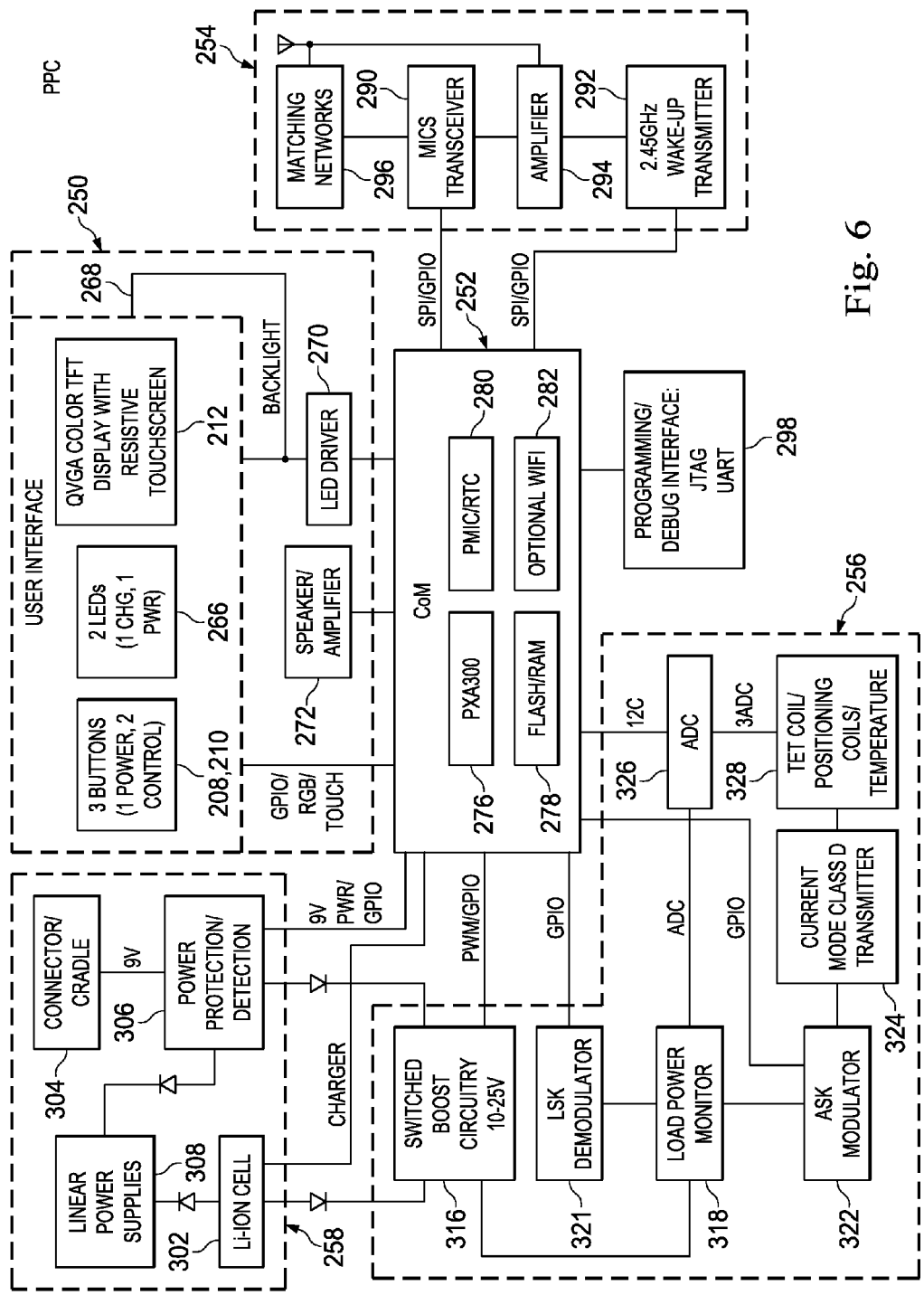
FIG. 6 is a block diagram of components of the example patient programmer charger of FIGS. 5A-5B in accordance with one embodiment of the present disclosure.

FIGS. 3A-3B, 4, 5A-5B, and 6 illustrate various example embodiments of the patient pocket programmer 22 (hereinafter referred to as patient programmer for simplicity) according to various aspects of the present disclosure. In more detail, FIGS. 3A-3B, 4 are directed to a patient programmer that is implemented as a pocket controller 104, and FIGS. 5A-5B and 6 are directed to a patient programmer that is implemented as a patient programmer charger (PPC) 106.

Referring now to FIGS. 3A and 3B, the pocket controller 104 comprises an outer housing 120 having an on-off switch 122, a user interface comprising a plurality of control buttons 124, and a display 126. In this embodiment, the housing 120 is sized for discreetness and may be sized to fit easily in a pocket and may be about the same size as a key fob. In one example, the housing 120 forming the pocket controller 104 has a thickness of less than about 1.5 inch, a width of less than about 1.5 inch, and a height of less than about 3 inches. In another example, the housing 120 forming the pocket controller 104 has a thickness of about 0.8 inch, a width of about 1.4 inch, and a height of about 2.56 inch. However, both larger and smaller sizes are contemplated.

In this example, the control buttons 124 include two adjustment buttons 128a, 128b, a select button 130, and an emergency off button (not shown, but disposed on a side of the housing 120 opposing the on-off switch 122). The two adjustment buttons 128a, 128b allow a user to scroll or highlight available options and increase or decrease values shown on the display 126. The select button 130 allows a user to enter the value or select the highlighted options to be adjusted by actuation of the adjustment buttons 128a, 128b. In this example, the buttons 128a, 128b are used to navigate to one of the three available functions: 1) electrical stimulation on/off, 2) control stimulation amplitude adjustment, and 3) electrical stimulation program selection. Once the desired function is highlighted, the select button is pushed to allow changes (i.e. change the stimulation amplitude, select a different stimulation program, or turn the electrical stimulation on or off). In some examples, the IPG control functions of the pocket controller 104 consist of these functions. The emergency off button is disposed for easy access for a patient to turn off stimulation from the IPG 102 if the IPG provides too much stimulation or stimulation becomes uncomfortable for the patient. Allowing the user to scroll through the plurality of options (also referred to herein as operational parameters) that can be adjusted via the pocket controller 104 provides the user the confidence to carry only the pocket controller 104 while away from home. Users may be reluctant to carry only a conventional controller that allows adjustment of only a single operational parameter out of fear that they may need to adjust a different operational parameter while away from a more full-featured controller.

In the embodiment shown, the display 126 is an LCD display arranged to convey information to the user regarding selectable options, present settings, operating parameters and other information about the IPG 102 or the pocket controller 104. In this example, the display 126 shows the pocket controller's battery status at 132, the IPG's battery status at 134, the IPG's on or off status at 136, the currently selected electrical stimulation program at 138, and the amplitude setting of the running electrical stimulation program at 140. Other types of displays are also contemplated.

FIG. 4 shows a block diagram of components making up the pocket controller 104. It includes a user interface 150, a control module 152, a communication module 154, and a power storing controller 156. The user interface 150 is comprised of the buttons 128a, 128b, 130 and the display 126 described above with reference to FIG. 3A.

As can be seen, the user interface 150 is in communication with the control module 152. The control module 152 comprises a processor 158, memory, an analog-digital converter 162, and a watch dog circuit 164. The processor 158 may include a microprocessor, a controller, a digital signal processor (DSP), an application specific integrated circuit (ASIC), a field programmable gate array (FPGA), discrete logic circuitry, or the like. The processor 158 is configured to execute code or instructions provided in the memory. Here, the memory is comprised of flash memory 166 and RAM memory 168. However, the memory may include any volatile or non-volatile media, such as a random access memory (RAM), read only memory (ROM), non-volatile RAM (NVRAM), electrically erasable programmable ROM (EEPROM), flash memory, and the like. In some embodiments, the memory stores sets of stimulation control parameters that are available to be selected for delivery through the communication module 154 to the IPG 102 for electrical stimulation therapy. The AD converter 162 performs known functions of converting signals and the WD 164 is arranged to time out when necessary, such as in an event where the software becomes stuck in a loop. In one embodiment, the control module 152 comprises integrated circuits disposed on a PC board.

The communication module 154 comprises a medical implant communication service (MICS) RF transceiver 172 used to communicate with the IPG 102 to communicate desired changes and to receive status updates from and relating to the IPG 102, such as battery status and any error information. As used herein, MICS refers to wireless communications in a frequency band ranging from about 402 MHz to about 405 MHz, which is dedicated for communications with implanted medical devices. In this example, the MICS RF transceiver 172 utilizes a loop antenna for the communications with the IPG 102. Other antennas, such as, for example, dipole, chip antennas, or other known in the art also may be used. The communication module 154 also includes a wake up transmitter 174, an amplifier 176, and matching networks 178. The wake up transmitter 174 operates on a high frequency and is configured to send a short signal burst to wake up the IPG 102 when it is in a power-saving mode. Once the IPG 102 is ready, a communications link can be established between the IPG 102 and pocket controller 104, and communications can then occur over the MICS transceiver 172 using a standard frequency for a medical device transmission. The matching networks 178 tunes the antenna for optimum transmission power for the frequency selected. The pocket controller 104 also includes a programming interface 182. This may be used during manufacturing to load an operating system and program the pocket controller 104.

The power storing controller 156 is configured to convert power to recharge one or more rechargeable batteries 180. The batteries 180 provide power to operate the pocket controller 104 allowing it to receive user inputs and transmit control signals to the IPG 102. Some embodiments use primary cell batteries instead of rechargeable batteries. As indicated above, this pocket controller 104 is part of a larger system that contains the PPC 106 with a rich feature set for controlling the IPG 102 and includes an integrated battery charger used to charge the IPG's battery. By providing both the pocket controller 104 and the PPC 106, the patient can have a small unobtrusive device to carry around as they go about their daily business and a larger more full featured device which they can use in the comfort and privacy of their homes.

The pocket controller 104 is not only comfortable to carry in a pocket, but can also be attached to a key ring, lanyard, or other such carrying device for ease of daily use. Its functions are a subset of functions found on the PPC 106, and permit a user to power stimulation from the IPG on and off (i.e., the IPG 102 remains on, but stimulation is toggled between the on state when the IPG 102 is emitting electrical pulses and the off state when the IPG 102 is not emitting electrical pulses but remains in the standby mode for additional communications from the pocket controller 104, the PPC 106, or both), select which electrical stimulation program to run, and globally adjust the amplitude of electrical pulses emitted in a series of electrical pulses emitted by the IPG 102. By limiting the functions of the pocket controller to those most commonly used on a daily basis, the device becomes much less intimidating to the patient, and allows it to be kept very small. By keeping the device small, such as about key fob size, it becomes unobtrusive and the patient is more comfortable with having and using an implanted device.

FIGS. 5A-5B show the PPC 106 in greater detail. FIG. 5A is a front view of the PPC and FIG. 5B is a top view of FIG. 5A. The PPC 106 performs all the same operating functions as the pocket controller 104, but includes additional operating functions making it a multi-function full-featured, advanced patient controller charger. In the embodiment shown, the PPC 106 provides a simple but rich feature set to the more advanced user, along with the charging functions.

The PPC 106 includes a controller-charger portion 200 and a coil portion 202 connected by a flexible cable 204 and sharing components as described below. The controller-charger portion 200 comprises an outer housing 206 having an on-off switch 208 on its side, a plurality of control buttons 210, and a display 212, and an emergency off button (not shown, but disposed on a side of the housing 206 opposing the on-off switch 208). In this embodiment, the control buttons 210 are icons on the display 212, and the display is a full color, touchscreen, graphical user interface. In addition, the controller-charger portion 200 includes a home button 214 configured to return the displayed images to a home screen. The controller-charger portion 200 is larger than the pocket controller 104 and in one embodiment is sized with a height greater than about 3 inches, a width greater than about 2.5 inches, and a thickness greater than about 0.8 inch. In another embodiment, the controller-charger portion is sized with a width of about 3.1 inches, a height of about 4.5 inches, and thickness of about 0.96 inches, although both larger and smaller sizes are contemplated.

In this example, the control buttons 210 allow a user to select a desired feature for control or further display. Particularly, the control buttons 210 enable functions of the PPC 106 that are the same as those of the pocket controller 104 (stimulation on/off, program stimulation amplitude adjustment, and stimulation program selection) along with additional features including: charging IPG battery, individual pulse stimulation amplitude adjustment that adjusts an amplitude of an individual pulse relative to the amplitude of an adjacent pulse in a series of pulses emitted by the IPG 102, stimulation program frequency adjustment, individual pulse width adjustment, detailed IPG status, detailed PPC status, PPC setup/configuration, a PPC battery status indicator, PPC to IPG communication status indicator, and other items and functions. The detailed IPG status may include, for example, IPG serial number and IPG software revision level. Detailed PPC status may include, for example, date and time setting, brightness control, audio volume and mute control, and PPC serial number and software revision level.

By having a pocket controller 104 that is limited to a plurality, such as only three controls (stimulation on/off, program amplitude adjust, and stimulation program selection), for example, a user can quickly and easily identify and select the features that are most commonly used. Features that are used less frequently, such as IPG recharge, are included on the full-featured PPC, but not the pocket controller 104. Features that are seldom accessed, or not accessed at all by some users, including individual pulse amplitude adjust, pulse width adjust, stimulation program frequency adjust, or serial number and software revision information, are also not included on the limited-feature pocket controller, but are included on the PPC. This allows the pocket controller to be significantly smaller, with a very simple and easy to user interface, as compared to systems that need to support all of these features.

Referring to the example shown in FIG. 5A, the touchscreen display 212 is arranged to convey information to the user regarding selectable options, current settings, operating parameters and other information about the IPG 102 or the PPC 106. In this example, the display 212 shows a MICS communication indicator 220, the PPC's battery status at 222, the IPG's battery status at 224, the IPG's on or off status at 226, the currently selected electrical stimulation program at 228, and the amplitude setting of the active electrical stimulation program at 230. In addition, the display 212 shows the frequency 232, the pulse width setting 234, a selectable status icon for accessing detailed PPC information 236, a selectable status icon for accessing detailed IPG information 238, and a selectable icon for enabling IPG charging 240. Selecting any single icon may activate another menu within that selected subject area. The controller-charger portion 200 may include a rechargeable battery whose charge status is shown by the PPC's battery status at 222.

The coil portion 202 is configured to wirelessly charge the batteries in the IPG 102. In use, the coil portion 202 is applied against the patient's skin or clothing externally so that energy can be inductively transmitted and stored in the IPG battery. As noted above, the coil portion 202 is connected with the integrated controller-charger portion 200. Accordingly, the controller-charger portion 200 can simultaneously display the current status of the coil portion 204, the battery power level of the IPG 102, as well as the battery power level of the PPC. Accordingly, controlling and charging can occur in a more simplistic, time-effective manner, where the patient can perform all IPG maintenance in a single sitting. In addition, since the most commonly used features of the PPC 106 are already functional on the pocket controller, the PPC 106 may be left at home when the user does not desire to carry the larger, more bulky PPC.

FIG. 6 shows a block diagram of the components making up the PPC 106. It includes a user interface 250, a control module 252, a communication module 254, an IPG power charging module 256, and a power storing module 258. The user interface 250 is comprised of the buttons 210 and the display 212 described above. In this embodiment however, the user interface 250 also includes one or more LEDs 266 signifying whether the PPC 106 is charging or powered on and a backlight 268 that illuminates the color display. In some embodiments, these LEDs may have colors symbolizing the occurring function. An LED driver 270 and a speaker or amplifier 272 also form a part of the user interface 250.

As can be seen, the user interface 250 is in communication with the control module 252. The control module 252 comprises a processor 276, memory 278, and a power management integrated circuit (PMIC)/real time clock (RTC) 280. In the example shown, the control module 252 also includes a Wi-Fi RF transceiver 282 that allows the PPC 106 to connect to a wireless network for data transfer. For example, it may permit doctor-patient interaction via the internet, remote access to PPC log files, remote diagnostics, and other information transfer functions. The PMIC 280 is configured to control the charging aspects of the PPC 106. The Wi-Fi transceiver 282 enables Wi-Fi data transfer for programming the PPC 106, and may permit wireless access to stored data and operating parameters. Some embodiments also include a Bluetooth RF transceiver for communication with, for example, a Bluetooth enabled printer, a keyboard, etc.

In one embodiment, the control module 252 also includes an AD converter and a watch dog circuit as described above with reference to the control module 252. Here, the memory 278 is comprised of flash memory and RAM memory, but may be other memory as described above. In some embodiments, the processor 276 is an embedded processor running a WinCE operating system (or any real time OS) with the graphics interface 250, and the memory 278 stores sets of stimulation control parameters that are available to be selected for delivery through the communication module 254 to the IPG 102 for electrical stimulation therapy. In one embodiment, the control module 252 comprises integrated circuits disposed on a PC board.

The communication module 254 comprises a MICS RF transceiver 290, a wake up transmitter 292, an amplifier 294, and matching networks 296. The communication module 254 may be similar to the communication module 154 discussed above, and will not be further described here. The PPC 206 also includes a programming interface 298 that may be used during manufacturing to load an operating system and program the PPC 206.

The power storing module 258 is configured to convert power to recharge one or more rechargeable batteries 302. In this embodiment, the batteries 302 are lithium-ion cells that provide power to operate the PPC 106 allowing it to receive user inputs, transmit control signals to, and charge the IPG 102. The power storing module 258 includes a connector 304 for connecting to a power source, a power protection detection circuit 306 for protecting the PPC from power surges, and linear power supplies 308 for assisting with the electric transfer to charge the batteries 302. As can be seen, the control module 252 aids with the charging and is configured to monitor and send the battery charge level to the user interface 250 for display. The connector 304 connects the PPC, directly or indirectly, to a power source (not shown) such as a conventional wall outlet for receiving electrical current. In some embodiments, the connector 304 comprises a cradle.

The power charging module 256 communicates with the control module 252 and is arranged to magnetically or inductively charge the IPG 102. In the embodiments shown, it is magnetically or inductively coupled to the IPG 102 to charge rechargeable batteries on the IPG 102. The charging module 256 includes components in both the controller-charger portion 200 and the coil portion 202 (FIGS. 5A-5B). It includes switch boost circuitry 316, a load power monitor 318, an LSK demodulator 321, a ASK modulator 322, a current mode transmitter 324, an ADC 326, and coils 328. As can be seen, the control module 252 aids with the charging and is configured to monitor and send the IPG battery charge level to the user interface 250 for display.

In this embodiment, the coils 328 are disposed in the coil portion 202 and are configured to create magnetic or inductive coupling with components in the IPG 102. Since the coil portion 202 is integrated with the controller-charger portion 200, both operate from a single battery 302. Accordingly, as can be seen by the circuitry, the battery 302 powers the control module 252 and all its associated components. In addition, the battery 302 powers the power charging module 256 for recharging the IPG 102.

Because the coil portion 202 is integrated with the controller-charger portion 200, the control module 252 provides a single control interface and a single user interface for performing both functions of controlling the IPG 102 and of charging the IPG 102. In addition, because the controller-charger portion 200 and the coil portion 202 are integrated, the controller-charger portion 200 simultaneously controls both the current status of the charger, the battery power level of the IPG 102, as well as the battery power level of the PPC. Accordingly, controlling and charging can occur in a more simplistic, time-effective manner, where the patient can perform all IPG maintenance in a single sitting. In addition, since the most commonly used features of the PPC 106 are already functional on the pocket controller, the PPC 106 may be left at home when the user does not desire to carry the larger, more bulky PPC.

Figure 7:
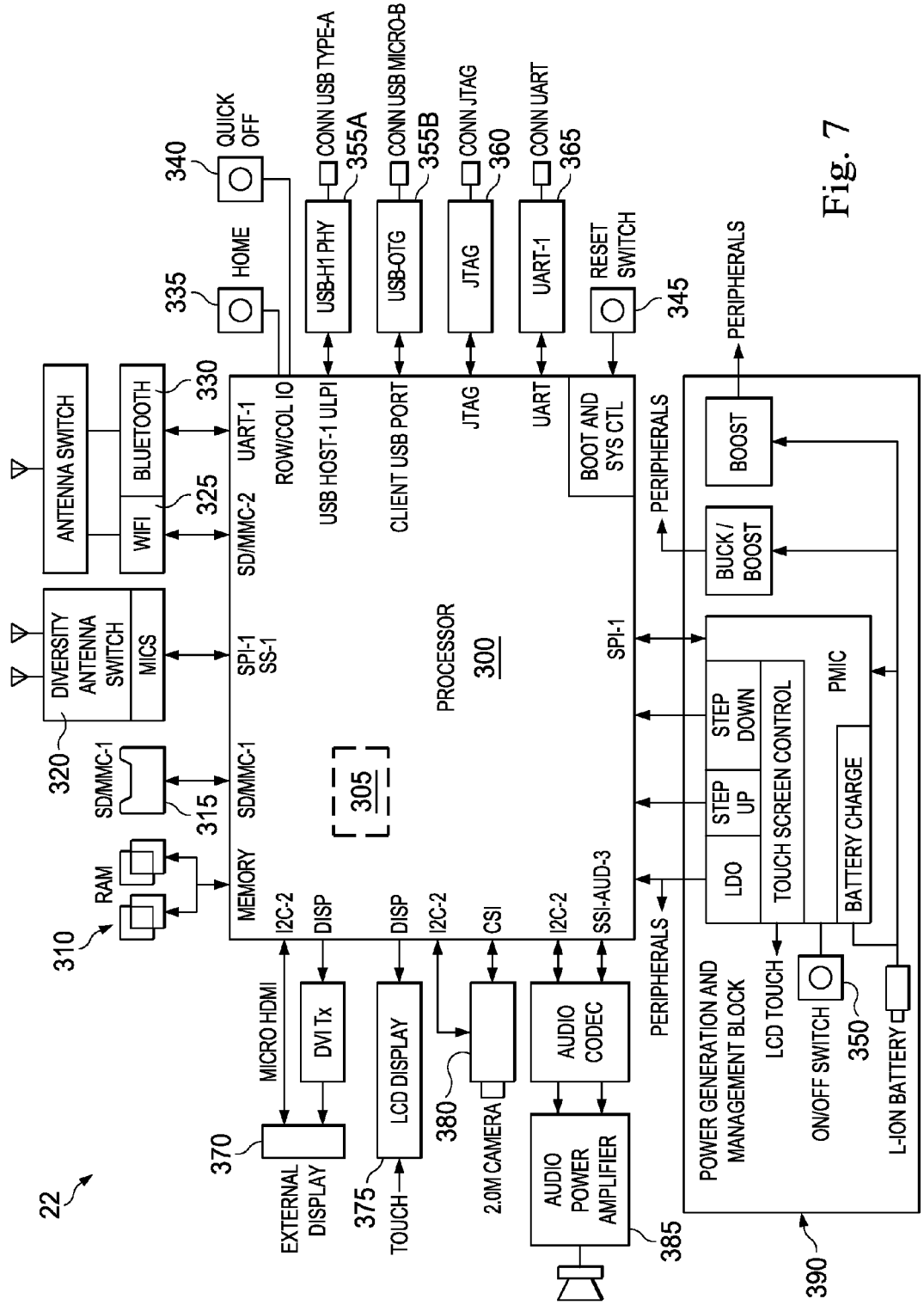
FIG. 7 is a block diagram of a clinician programmer according to one embodiment of the present disclosure.

FIG. 7 shows a block diagram of one example embodiment of a clinician programmer (CP), for example the CP 22 shown in FIG. 2B. The CP 22 includes a printed circuit board ("PCB") that is populated with a plurality of electrical and electronic components that provide power, operational control, and protection to the CP 22. With reference to FIG. 7, the CP includes a processor 300. The processor 300 is a controller for controlling the CP 22 and, indirectly, the IPG 20 as discussed further below. In one construction, the processor 300 is an applications processor model i.MX515 available from Freescale Semiconductor. More specifically, the i.MX515 applications processor has internal instruction and data cashes, multimedia capabilities, external memory interfacing, and interfacing flexibility. Further information regarding the i.MX515 applications processor can be found in, for example, the "IMX510EC, Rev. 4" data sheet; dated August 2010; published by Freescale Semiconductor at www.freescale.com, the content of the data sheet being incorporated herein by reference. Of course, other processing units, such as other microprocessors, microcontrollers, digital signal processors, etc., can be used in place of the processor 300.

The CP 22 includes memory, which can be internal to the processor 300 (e.g., memory 305), external to the processor 300 (e.g., memory 310), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 300 executes software that is capable of being stored in the RAM (e.g., during execution), the ROM (e.g., on a generally permanent basis), or another non-transitory computer readable medium such as another memory or a disc. The CP 22 also includes input/output ("I/O") systems that include routines for transferring information between components within the processor 300 and other components of the CP 22 or external to the CP 22.

Software included in the implementation of the CP 22 is stored in the memory 305 of the processor 300, memory 310 (e.g., RAM or ROM), or external to the CP 22. The software includes, for example, firmware, one or more applications, program data, one or more program modules, and other executable instructions. The processor 300 is configured to retrieve from memory and execute, among other things, instructions related to the control processes and methods described below for the CP 22. For example, the processor 300 is configured to execute instructions retrieved from the memory 140 for establishing a protocol to control the IPG 20.

One memory shown in FIG. 7 is memory 310, which can be a double data rate (DDR2) synchronous dynamic random access memory (SDRAM) for storing data relating to and captured during the operation of the CP 22. In addition, a secure digital (SD) multimedia card (MMC) can be coupled to the CP for transferring data from the CP to the memory card via slot 315. Of course, other types of data storage devices can be used in place of the data storage devices shown in FIG. 7.

The CP 22 includes multiple bi-directional radio communication capabilities. Specific wireless portions included with the CP 22 are a Medical Implant Communication Service (MICS) bi-direction radio communication portion 320, a Wi-Fi bi-direction radio communication portion 325, and a Bluetooth bi-direction radio communication portion 330. The MICS portion 320 includes a MICS communication interface, an antenna switch, and a related antenna, all of which allows wireless communication using the MICS specification. The Wi-Fi portion 325 and Bluetooth portion 330 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP 22.

The CP 22 includes three hard buttons: a "home" button 335 for returning the CP to a home screen for the device, a "quick off" button 340 for quickly deactivating stimulation IPG, and a "reset" button 345 for rebooting the CP 22. The CP 22 also includes an "ON/OFF" switch 350, which is part of the power generation and management block (discussed below).

The CP 22 includes multiple communication portions for wired communication. Exemplary circuitry and ports for receiving a wired connector include a portion and related port for supporting universal serial bus (USB) connectivity 355, including a Type-A port and a Micro-B port; a portion and related port for supporting Joint Test Action Group (JTAG) connectivity 360, and a portion and related port for supporting universal asynchronous receiver/transmitter (UART) connectivity 365. Of course, other wired communication standards and connectivity can be used with or in place of the types shown in FIG. 7.

Another device connectable to the CP 22, and therefore supported by the CP 22, is an external display. The connection to the external display can be made via a micro High-Definition Multimedia Interface (HDMI) 370, which provides a compact audio/video interface for transmitting uncompressed digital data to the external display. The use of the HDMI connection 370 allows the CP 22 to transmit video (and audio) communication to an external display. This may be beneficial in situations where others (e.g., the surgeon) may want to view the information being viewed by the healthcare professional. The surgeon typically has no visual access to the CP 22 in the operating room unless an external screen is provided. The HDMI connection 370 allows the surgeon to view information from the CP 22, thereby allowing greater communication between the clinician and the surgeon. For a specific example, the HDMI connection 370 can broadcast a high definition television signal that allows the surgeon to view the same information that is shown on the LCD (discussed below) of the CP 22.

The CP 22 includes a touchscreen I/O device 375 for providing a user interface with the clinician. The touchscreen display 375 can be a liquid crystal display (LCD) having a resistive, capacitive, or similar touch-screen technology. It is envisioned that multitouch capabilities can be used with the touchscreen display 375 depending on the type of technology used.

The CP 22 includes a camera 380 allowing the device to take pictures or video. The resulting image files can be used to document a procedure or an aspect of the procedure. For example, the camera 380 can be used to take pictures of barcodes associated with the IPG 20 or the leads 120, or documenting an aspect of the procedure, such as the positioning of the leads. Similarly, it is envisioned that the CP 22 can communicate with a fluoroscope or similar device to provide further documentation of the procedure. Other devices can be coupled to the CP 22 to provide further information, such as scanners or RFID detection. Similarly, the CP 22 includes an audio portion 385 having an audio codec circuit, audio power amplifier, and related speaker for providing audio communication to the user, such as the clinician or the surgeon.

The CP 22 further includes a power generation and management block 390. The power generation and management block 390 has a power source (e.g., a lithium-ion battery) and a power supply for providing multiple power voltages to the processor, LCD touchscreen, and peripherals.

Figure 8:
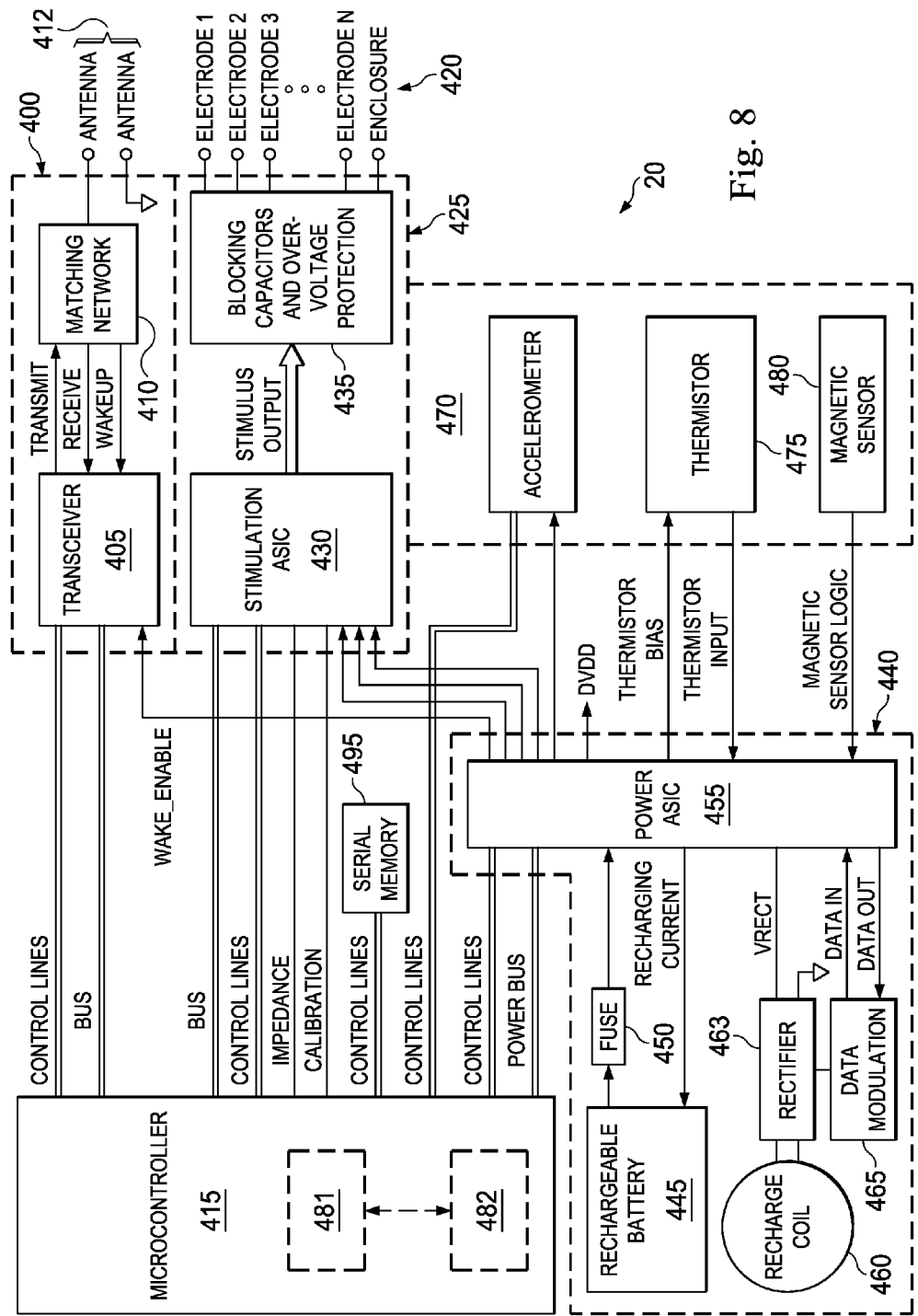
FIG. 8 is a block diagram of an implantable pulse generator according to one embodiment of the present disclosure.

FIG. 8 shows a block diagram of an example embodiment of an IPG, for example an embodiment of the IPG 20 shown in FIG. 2B. The IPG 20 includes a printed circuit board ("PCB") that is populated with a plurality of electrical and electronic components that provide power, operational control, and protection to the IPG 20. With reference to FIG. 8, the IPG 20 includes a communication portion 400 having a transceiver 405, a matching network 410, and antenna 412. The communication portion 400 receives power from a power ASIC (discussed below), and communicates information to/from the microcontroller 415 and a device (e.g., the CP 22) external to the IPG 20. For example, the IPG 20 can provide bi-direction radio communication capabilities, including Medical Implant Communication Service (MICS) bi-direction radio communication following the MICS specification.

The IPG 20, as previously discussed, provides stimuli to electrodes 150 of an implanted medical electrical lead 110. As shown in FIG. 8, N electrodes 150 are connected to the IPG 20. In addition, the enclosure or housing 420 of the IPG 20 can act as an electrode. The stimuli are provided by a stimulation portion 425 in response to commands from the microcontroller 415. The stimulation portion 425 includes a stimulation application specific integrated circuit (ASIC) 430 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, Flash, etc. The stimulation ASIC 430 can include a processor, memory, and firmware for storing preset pulses and protocols that can be selected via the microcontroller 415. The providing of the pulses to the electrodes 150 is controlled through the use of a waveform generator and amplitude multiplier of the stimulation ASIC 430, and the blocking capacitors and overvoltage protection circuitry of the stimulation portion 425, as is known in the art. The stimulation portion 425 of the IPG 20 receives power from the power ASIC (discussed below). The stimulation ASIC 430 also provides signals to the microcontroller 415. More specifically, the stimulation ASIC 430 can provide impedance values for the channels associated with the electrodes 150, and also communicate calibration information with the microcontroller 415 during calibration of the IPG 20.

The IPG 20 also includes a power supply portion 440. The power supply portion includes a rechargeable battery 445, fuse 450, power ASIC 455, recharge coil 460, rectifier 463 and data modulation circuit 465. The rechargeable battery 445 provides a power source for the power supply portion 440. The recharge coil 460 receives a wireless signal from the PPC 135. The wireless signal includes an energy that is converted and conditioned to a power signal by the rectifier 463. The power signal is provided to the rechargeable battery 445 via the power ASIC 455. The power ASIC 455 manages the power for the IPG 20. The power ASIC 455 provides one or more voltages to the other electrical and electronic circuits of the IPG 155. The data modulation circuit 465 controls the charging process.

The IPG also includes a magnetic sensor 480. The magnetic sensor 480 provides a "hard" switch upon sensing a magnet for a defined period. The signal from the magnetic sensor 480 can provide an override for the IPG 20 if a fault is occurring with the IPG 20 and is not responding to other controllers. The magnetic sensor 480 can also be used to turn on and off stimulation.

The IPG 20 is shown in FIG. 8 as having a microcontroller 415. Generally speaking, the microcontroller 415 is a controller for controlling the IPG 20. The microcontroller 415 includes a suitable programmable portion 481 (e.g., a microprocessor or a digital signal processor), a memory 482, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2×32, MSP430G2× 02 MIXED SIGNAL MICROCONTROLLER" data sheet; dated December 2010, published by Texas Instruments at www.ti.com; the content of the data sheet being incorporated herein by reference.

The IPG 20 includes memory, which can be internal to the control device (such as memory 482), external to the control device (such as serial memory 495), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 481 executes software that is capable of being stored in the RAM (e.g., during execution), the ROM (e.g., on a generally permanent basis), or another non-transitory computer readable medium such as another memory or a disc.

Software included in the implementation of the IPG 20 is stored in the memory 482. The software includes, for example, firmware, one or more applications, program data, one or more program modules, and other executable instructions. The programmable portion 481 is configured to retrieve from memory and execute, among other things, instructions related to the control processes and methods described below for the IPG 20. For example, the programmable portion 481 is configured to execute instructions retrieved from the memory 482 for sweeping the electrodes in response to a signal from the CP 22.

The PCB also includes a plurality of additional passive and active components such as resistors, capacitors, inductors, integrated circuits, and amplifiers. These components are arranged and connected to provide a plurality of electrical functions to the PCB including, among other things, filtering, signal conditioning, or voltage regulation, as is commonly known.

Figure 9:
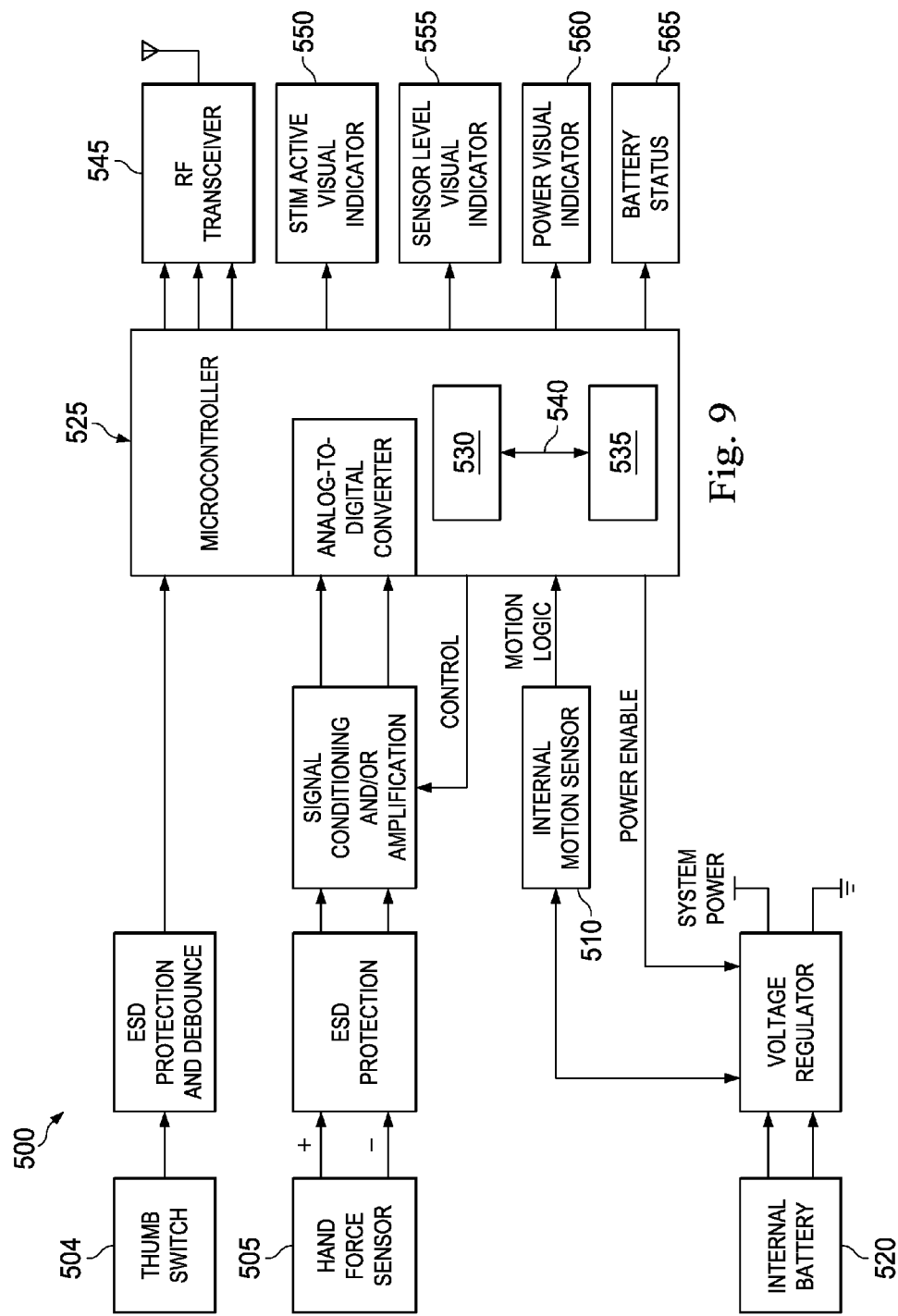
FIG. 9 is a diagrammatic block diagram of a patient feedback device according to an embodiment of the present disclosure.
Figure 10A:
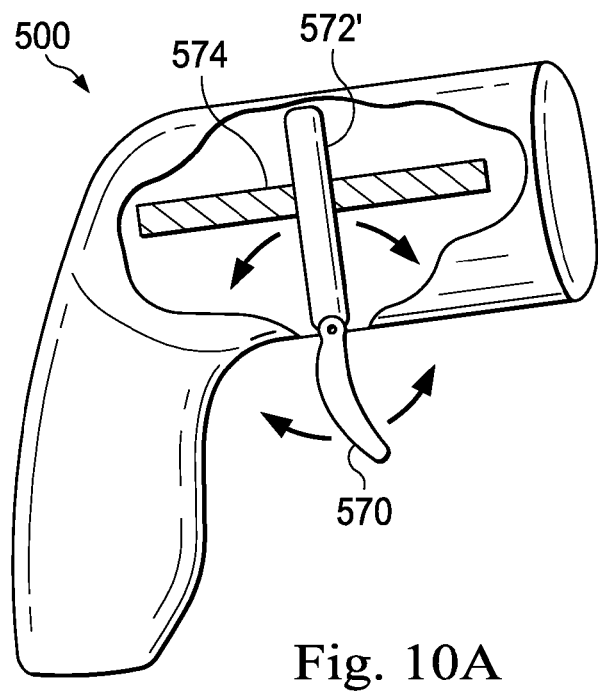
FIGS. 10A and 10B are exterior views of the patient feedback device according to embodiments of the present disclosure.
Figure 10B:
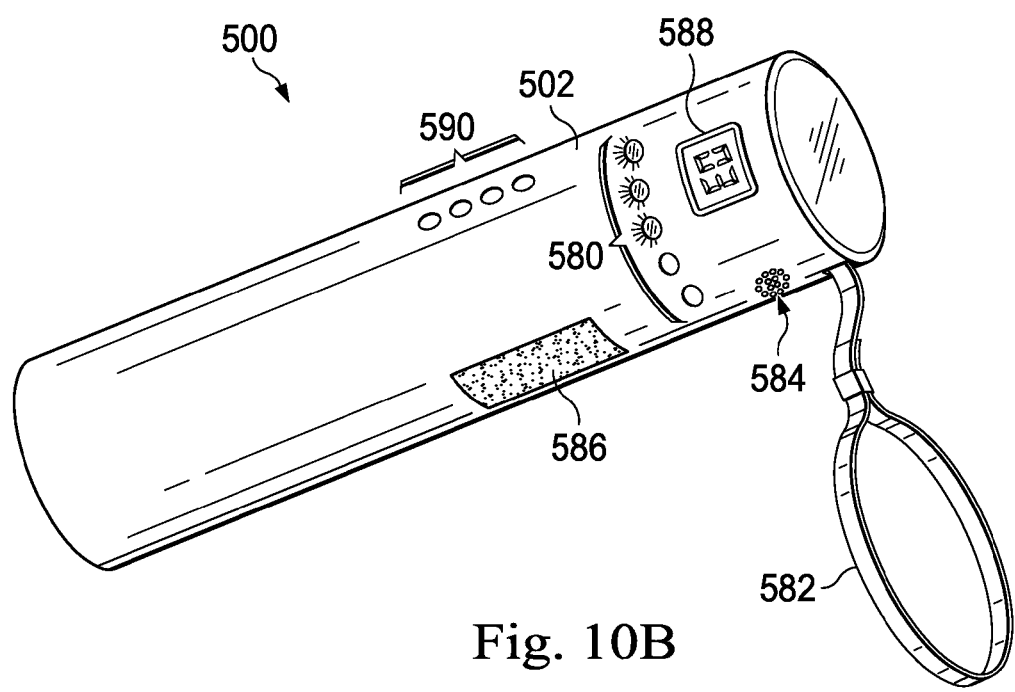

FIG. 9 is a block diagram of an exemplary handheld patient feedback device or patient feedback tool (hereinafter interchangeably referred to as PFD or PFT) 500 for use in a neurostimulation system, and FIGS. 10A and 10B are diagrammatic illustrations of the PFT 500 according to various example embodiments. With reference to FIGS. 9 and 10A-10B, the PFT 500 includes a housing 502 which may have one or more of a sensor, a controller, and/or a communication port connected thereto. The construction of the PFT 500 shown in FIG. 9 includes two inputs 504 and 505 in communication with the housing 502 of the device 500 and one input 510 internal to the housing 502. One of the external inputs 504 is a binary ON/OFF switch, for example activated by the patient's thumb, to allow the patient to immediately deactivate stimulation. Input 504 may be coupled to the controller 525 via electrostatic discharge (ESD) protection and/or debouncing circuits. The second input 505 includes a force sensor sensing the pressure or force exerted by the patient's hand. Input/sensor 505 may be coupled to the controller 525 via ESD protection, signal conditioning, and/or signal amplification circuits. The sensed parameter can be either isotonic (constant force, measuring the distance traversed) or isometric (measured force, proportional to pressure applied by patient). The resulting signal from the sensor 505 is analog and, therefore, after the signal is conditioned and/or amplified, it can be passed to microcontroller 525 via an analog-to-digital converter.

The internal input 510 for the PFT 500 may be a motion sensor. The sensor 510, upon detecting motion, initiates activation of the PFT 500. The device 500 stays active until movement is not detected by the sensor 510 for a time period, which in various constructions may be between one second and five minutes. Power is provided by an internal battery 520 that can be replaceable and/or rechargeable, which in various constructions has an approximately three hour life under continuous use. As discussed below, a motion sensor such as sensor 510 can also be used to obtain feedback from the patient regarding paresthesia.

The processing of the inputs from the sensors 504 and 505 takes place in a controller, such as a microcontroller 525. An exemplary microcontroller capable of being used with the invention is microcontroller 525, which includes a suitable programmable portion 530 (e.g., a microprocessor or a digital signal processor), a memory 535, and a bus 540 or other communication lines. Output data of the microcontroller 525 is sent via a Bluetooth bi-direction radio communication port 545 to the CP (clinician programmer). The Bluetooth portion 545 includes a Bluetooth communication interface, an antenna switch, and a related antenna, all of which allows wireless communication following the Bluetooth Special Interest Group standard. Other forms of wired and wireless communication between the PFT 500 and other components of the system including the CP are also possible. Other outputs may include indicators (such as light-emitting diodes) for communicating stimulation activity 550, sensor activation 555, device power 560, and battery status 565.

The housing 502 of the PFT 500 may be cylindrical in shape, and in one particular construction the cylinder is approximately 35 mm in diameter and 80 mm in length. In other constructions the cylinder is larger or smaller in diameter and/or length, for example in order to accommodate hands of varying sizes. In various constructions the diameter can range from 20 to 50 mm and the length from 30 to 120 mm, although other sizes above and below these ranges are also possible.

Furthermore, the shape of the PFT 500 can be other than a circular cross-section, for example oval, square, hexagonal, or other shape. Still further, the cross-section of the PFT 500 can vary along its length, for example being cylindrical in some portions and oval, square, hexagonal or other shape(s) in other portions. In yet other constructions, the PFT 500 has a spherical, toroid, or other shape.

The housing 502 may be made from a resilient material such as rubber or plastic with one or more sensor 505 coupled to or supported by the housing 502. The manner in which the sensor 505 is coupled to the housing 502 depends on the type of sensor that is employed, as discussed below. Thus, when the patient applies a force to the housing 502, the sensor 505 generates a signal that generally is proportional to the degree of force applied. Although the discussion herein mentions the patient using his or her hand to generate force to squeeze the housing 502 of the PFT 500, in various constructions the patient may instead use other body parts, such as the mouth or foot, to generate force. More generally, the patient can generate feedback by a physical action, usually a force applied by the hand or other body part, but the physical action can include other movements, such as movement of the patient's eyes, head, or hands, to generate a feedback signal.

After the signal is generated, it is transmitted from the sensor 505 to the controller 525. The controller 525 processes the signal and, based on one or more such signals from the sensor 505, the controller 525 generates another signal that is to be transmitted to the CP. The controller 525 sends the signal to be transmitted to the communication port 545 of the PFT 500 from which it is then transmitted to the CP or other external device. As discussed further below, the signal can be transmitted from the communication port 545 to the CP using various wired or wireless methods of communication.

In various constructions, an isotonic force sensor may include a sensor that measures the distance traveled by the sensor with relatively constant force applied by the patient. Isotonic force sensors may include a trigger 570 (See FIG.

10A) or other lever mechanism coupled to a wiper 572 that moves along a rheostat 574 or across a series of detectors. Exemplary detectors include electrical contacts or optical detectors, such as photodiodes. In other constructions, an isometric force sensor may include a strain gauge, a piezoelectric device, or a pressure sensor, each of which measures force that is proportional to the pressure applied to the PFT 500 by the patient, generally with only a small amount of travel or shape change to the sensor.

Both the isotonic and isometric sensors generate an electrical signal that is proportional to the force that is applied to the sensor. An isometric force sensor may be incorporated into a relatively stiff object such that only slight deformation of the object is needed to register a change in force. In still other constructions, the force sensor may include a combination of elements, such as a trigger or other lever that experiences increasing resistance or pressure as the travel distance increases. For example, increasing resistance or pressure can be created by attaching a relatively stiff spring to the lever or wiper mechanism to increase resistance as the lever or wiper is moved.

In some constructions (e.g. as shown in FIG. 10B), the PFT 500 includes a feedback mechanism 580 that indicates to the patient the amount of force that is detected by the force sensor 505. The feedback mechanism 580 may include one or more of a visual, audible, or tactile feedback mechanism that is used to indicate to the patient the degree to which the sensor 505 has been activated, e.g., how much force has been applied or how much the lever or wiper mechanism has traveled. The feedback mechanism gives the patient a sense of whether their activation of the sensor 505 is being detected at what the patient feels is the correct level and to give the patient a means to make their activation of the sensor 505 more consistent.

Visual feedback mechanisms 580 can include a series of lights (e.g. LEDs) or a digital readout (e.g. a numerical display); audible feedback can include sounds that vary in amplitude (volume) and/or tone; and tactile feedback mechanisms can include vibration of the PFT 500 and/or altering the shape of the surface of the PFT 500 (e.g. raising of one or more structures such as dots to form Braille-type patterns) in a location that is capable of contacting the patient's skin. Using a combination of feedback modalities will benefit patients who have sensory impairments, including, e.g., impaired hearing and/or sight.

The feedback can include a semi-quantitative indication of the patient's response, e.g. including a variety of (e.g. 1-5 or 1-10) intensity levels to indicate a relative degree of force applied by the patient. The patient will then be able to see, hear, and/or feel the level of force that is sensed by the sensor 505 of the PFT 500, to help the patient confirm that their response to the stimulus was received, as well as the degree of response that was registered. The correlation between the level of force applied and the output of the feedback mechanism 580 can be calibrated separately for each patient during an initial calibration session.

To facilitate gripping of the PFT 500, the housing 502, in certain constructions, may be covered with one or more surfaces, textures, or materials to improve grip, such as grooves, stipples, indentations, rubber, or plastic, and may include a wrist strap 582 to keep the PFT 500 from falling if it is dropped by the patient.

The PFT 500, in some constructions, may also include a connection feedback mechanism, particularly where the PFT 500 is in wireless communication with the CP. The connection feedback mechanism can include one or more of a visual, audible, or tactile mechanism to inform the patient and/or medical personnel of whether the PFT 500 is maintaining a connection with the CP, the strength of the connection, and/or if the connection has been lost. For example, the PFT 500 may emit a signal (e.g. light, sound, and/or tactile) at regular (e.g. one minute) intervals to confirm that communication is still maintained.

Conversely, the PFT 500 may emit such a signal only if communication is lost. In some constructions, the PFT 500 may tolerate brief intervals in which the signal is lost (e.g. a predetermined time, generally between 0.1-100 sec) before the patient is warned of a possible lost connection. In various constructions, the controller 525 of the PFT 500 includes memory that permits buffering of a limited amount of data, which can be used to accumulate data prior to sending to the CP and which can hold data during brief intervals in which the connection is lost. In various constructions, if communication between the PFT 500 and the CP is lost for more than a predetermined interval of time, then the CP stops stimulation of electrodes until a connection with the PFT 500 is reestablished.

Thus, according to various constructions, the PFT 500 may include one or more of: a sound generating mechanism 584 (e.g. a speaker); a tactile mechanism 586 such as a vibration device and/or a mechanism for creating a raised pattern; a digital numerical readout 588 (e.g. LED or LCD display); and one or more indicator lights 590 (e.g. a series of LEDs); which may be employed to provide feedback to the patient regarding the force being applied and/or communication status.

Various types of sensing mechanisms can be used for the sensor 505, which would depend in part on the type of housing 502 that is used with the PFT 500. For example, if the housing 502 is a sealed, flexible compartment (e.g. a ball or other object filled with gel, air, or liquid) a piezoelectric-based pressure sensing mechanism can be used as the sensor 505 in order to measure changes in pressure when the patient squeezes or relaxes his/her grip on the PFT 500. Alternatively, a rheostat 574 or other linear sensing mechanism can be used with a pistol grip style PFT 500 design (FIG. 10A), where a trigger 570 is coupled to a wiper 572 that moves across the rheostat 574 or other linear sensor.

Figure 11A:
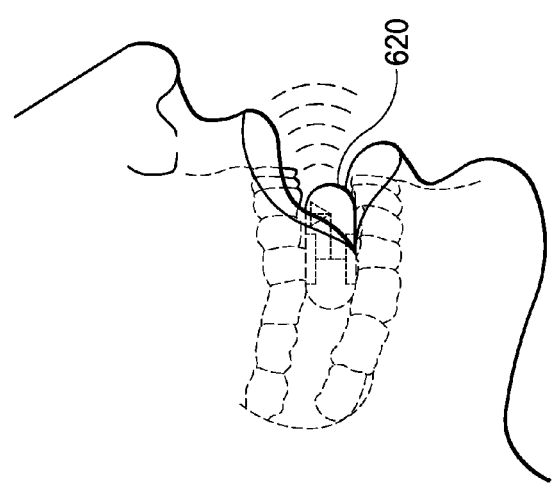
FIG. 11A is a side view of a patient-feedback device inserted in the mouth of a patient according to an embodiment of the present disclosure.
Figure 11B:
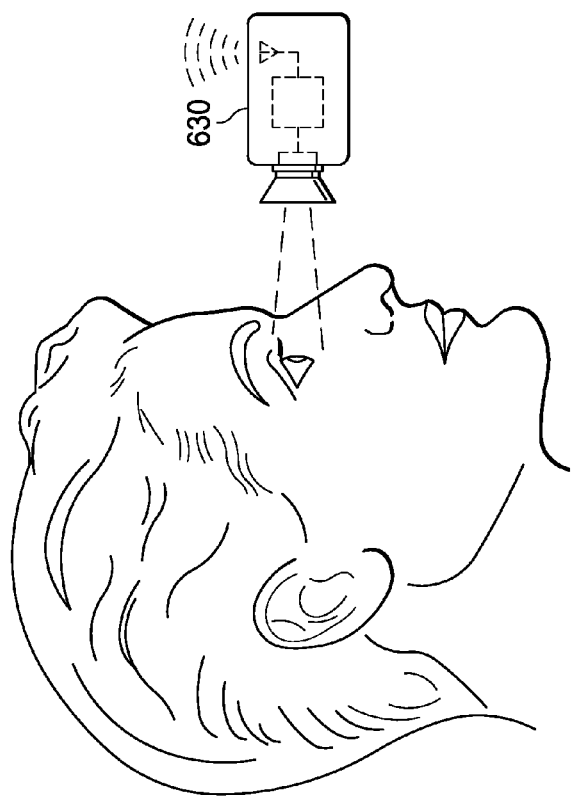
FIG. 11B is a side view of a patient-feedback device with optical sensing according to an embodiment of the present disclosure.
Figure 11C:
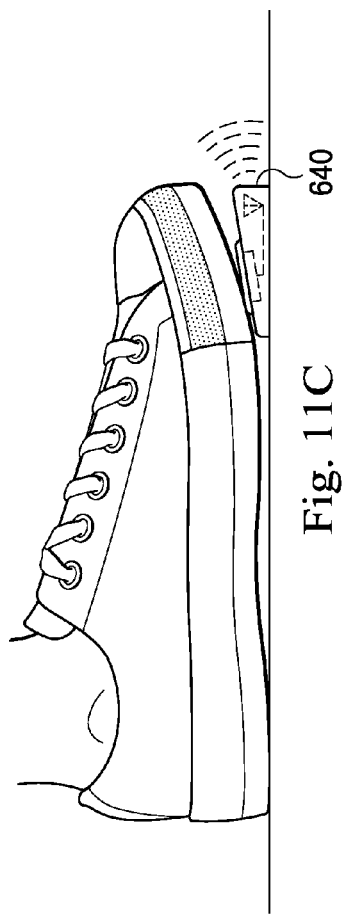
FIG. 11C is a side view of a patient-feedback device activated by a foot of a patient according to an embodiment of the present disclosure.

FIGS. 11A-11C illustrate other embodiments of the PFT for receiving patient feedback. More specifically, FIG. 11A shows a mouth-piece 620 that is inserted into the mouth of the patient. The user provides feedback by biting the mouth-piece. FIG. 11B shows an optical sensor 630 (such as a camera and related image processing software) that detects visual cues from a patient. An example visual cue may be the blinking of the patient's eyes. FIG. 11C shows a foot pedal 640 that receives input through the patient's manipulation of a switch and/or sensor with his foot. In some constructions, the PFT 500 includes one or more accelerometers (such as the motion sensor 510), and the patient provides feedback by moving the PFT 500 in various distinct patterns that are recognized by the controller 525 of the PFT 500 or by the CP.

It is also envisioned that the patient may provide feedback directly to the CP. In various constructions, the patient is trained to use the particular feedback device (e.g. the PFT 500 or the CP as applicable) in order to properly inform the CP of the patient's reaction to stimuli as they are applied to the IPG in the patient. In particular constructions, the CP is programmed to learn the patient's response times and/or the magnitude of the patient's responses in order to obtain a profile of the patient's reaction to various stimuli, as discussed above.

Figure 12:
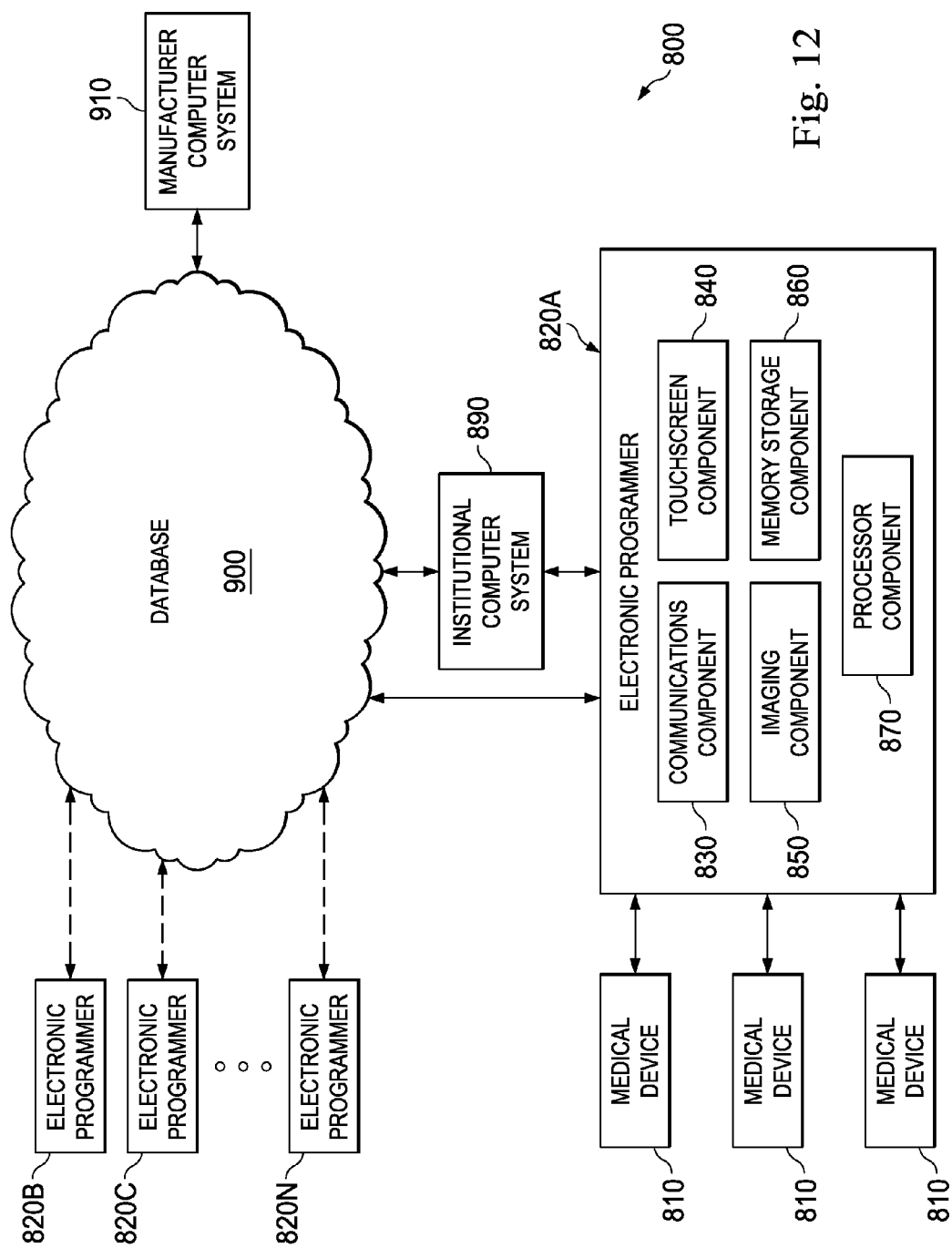
FIG. 12 is a simplified block diagram of a medical system/infrastructure according to various aspects of the present disclosure.

Referring now to FIG. 12, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above. For example, the medical devices 810 may be a pulse generator (e.g., the IPG discussed above), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIGS. 2B and 7. In other embodiments, the electronic programmer 820A may be a patient programmer discussed above with reference to FIGS. 2B-6. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 12 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, various types of data may be uploaded from the electronic programmer 820A to the database 900. The data saved in the database 900 may thereafter be downloaded by any of the other electronic programmers 820B-820N communicatively coupled to it, assuming the user of these programmers has the right login permissions.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

Figure 13:
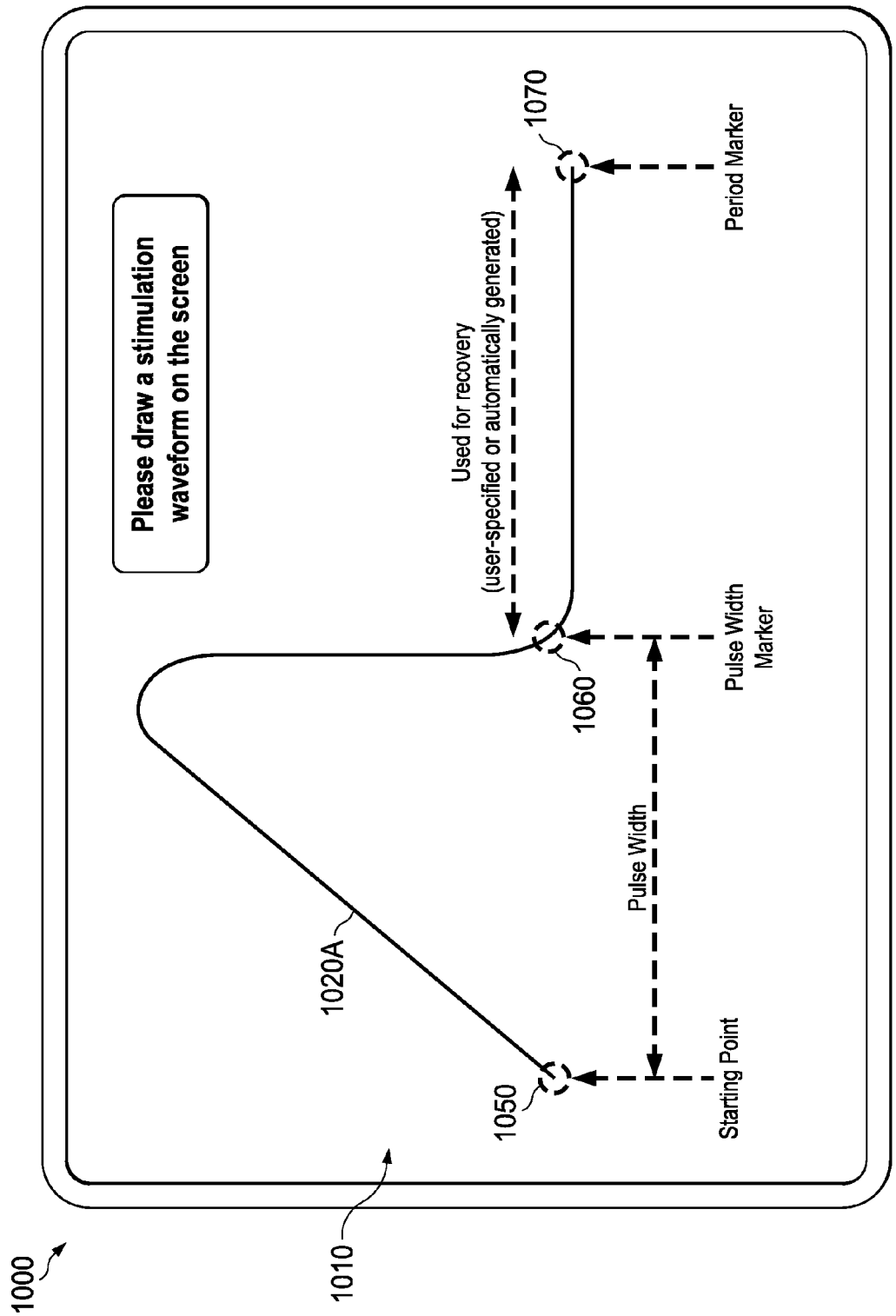
FIGS. 13-17 and 19-20 illustrates a graphical user interface on an electronic programmer according to various aspects of the present disclosure.
Figure 14:
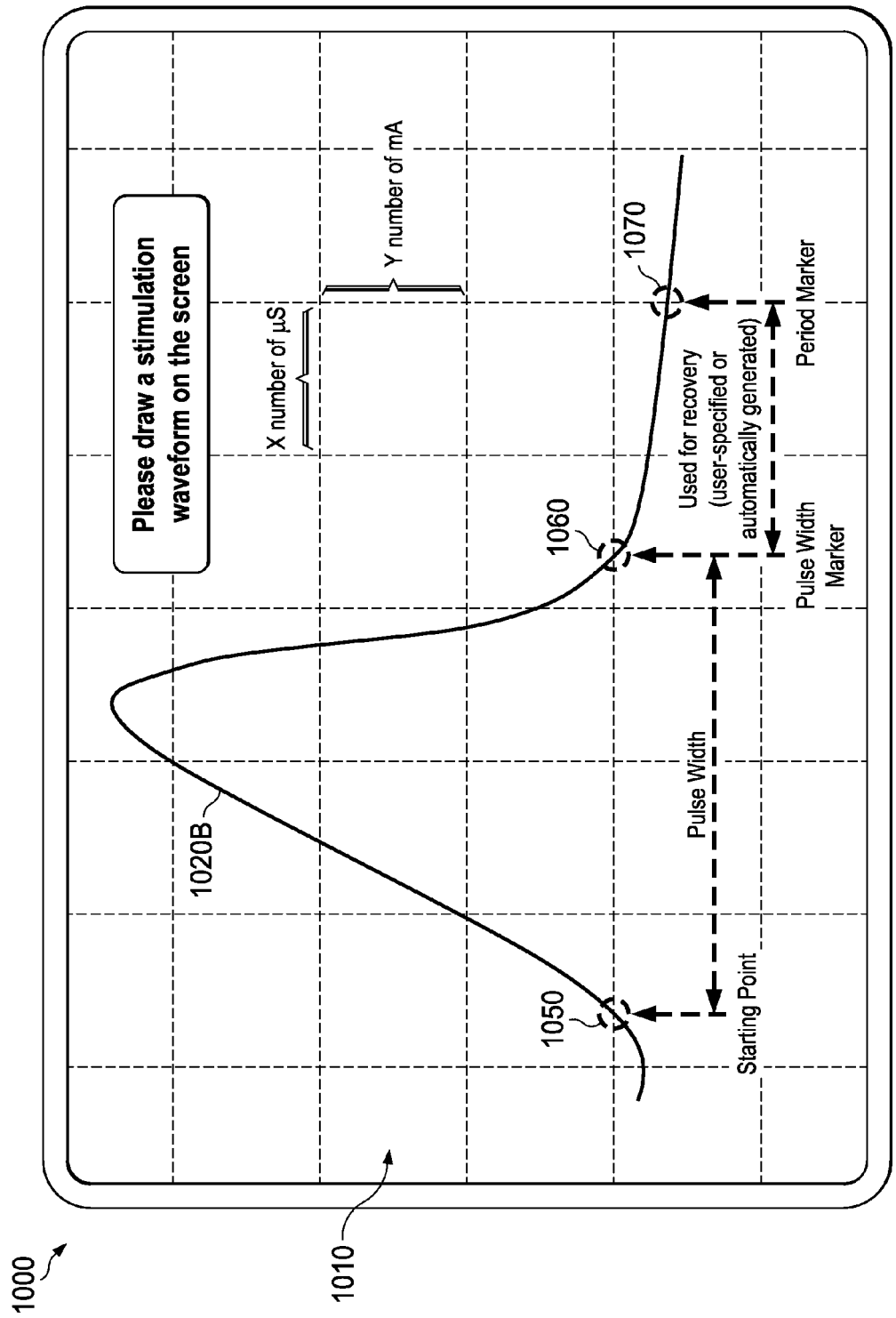

FIGS. 13-14 illustrate how a user such as a clinician or another healthcare professional can generate a stimulation waveform having an arbitrary shape. Traditionally, the stimulation waveform in stimulation therapy has a rectangular shape. However, the rectangular shape may or may not deliver the most effective stimulation therapy. According to various aspects of the present disclosure, the clinician programmer may allow its user (e.g., a healthcare professional) to define a more customized stimulation waveform, where the shape of the waveform can be defined by the user. For the purposes of the present disclosure, the custom-defined waveform having an arbitrary shape may also be referred to as a user-supplied waveform. The user-supplied waveform may be defined by the user directly, or it may be created by someone else and is used by the user to define the custom waveform.

As shown in FIG. 13, an electronic programmer 1000 may display a message prompting or informing the healthcare professional that he/she may enter a custom or user-defined stimulation waveform via a graphical user interface 1010 of the electronic programmer 1000. The electronic programmer 1000 may be a clinician programmer, for example the clinician programmer 22 discussed above with reference to FIGS. 2B and 7, or the electronic programmer 820A-N (implemented as a clinician programmer) discussed above with reference to FIG. 12. The graphical user interface 1010 is displayed via the touchscreen I/O device 375 of the clinician programmer 22 discussed above with reference to FIG. 7. The message displayed on the user interface 1010 may read, as an example, "Please draw a custom stimulation waveform on the screen."

The healthcare professional (hereinafter interchangeably referred to as the "user") may sketch or draw (e.g., via his finger or a stylus) a custom stimulation waveform via the graphical user interface 1010. For example, the user may use his/her finger or a stylus to draw a waveform 1020A as shown in FIG. 13 or a waveform 1020B as shown in FIG. 14. Since the waveforms 1020A and 1020B are drawn manually by the user, they are not confined to a specific shape such as a rectangular shape. Instead, the waveforms 1020A or 1020B may be drawn with an arbitrary shape, and different users may draw different waveforms (and the same user may draw different waveforms too). These waveforms may be referred to as hand-drawn waveforms, even though they may or may not be actually drawn by a hand of the user (e.g., they may be drawn via a stylus).

From the waveforms 1020A or 1020B drawn on the user interface 1010, one or more custom or arbitrarily-shaped waveform may be defined or derived. For example, given the waveforms 1020A or 1020B, the user may identify a desired starting point 1050, a pulse width marker 1060, and a period marker 1070 of a user-supplied waveform. In some embodiments, the user may touch (or long press) a portion of the graphical user interface 1010 corresponding to a first point on the waveform 1020A/1020B, and mark that as the starting point marker 1050 of the user-supplied waveform. The user may also touch (or long press) a portion of the graphical user interface 1010 corresponding to a second point on the waveform 1020A/1020B, and mark that as the pulse width marker 1060 of the user-supplied waveform. The user may further touch (or long press) a portion of the graphical user interface 1010 corresponding to a third point on the waveform 1020A/1020B, and mark that as the period width marker 1070 of the user-supplied waveform.

As its name implies, the pulse width marker 1060 marks the pulse width of the user-supplied waveform 1020A/1020B, which is the distance or separation between the starting point 1050 and the pulse width marker 1060. Similarly, the period width marker 1070 helps define the period of the user-supplied waveform 1020A/1020B, which is the distance or separation between the starting point 1050 and the period marker 1070. It is understood that the frequency of the user-supplied waveform can be calculated based on the period, and thus the period marker 1070 may be referred to as a frequency marker as well.

Note that the user is given flexibility in choosing the exact starting point 1050, pulse width marker 1060, and the period marker 1070. For example, as shown in FIG. 14, the user may designate a point after the very beginning of a hand-drawn waveform 1020B as the starting point 1050 of the user-supplied waveform. Similarly, the user may designate a point that is before the very last of the hand-drawn waveform 1020B as the period marker 1070. Furthermore, the user may freely move (e.g., by holding and dragging) any one of the starting point 1050, pulse width marker 1060, and the period marker 1070 on the waveform 1020A/1020B. As the starting point 1050, pulse width marker 1060, and the period marker 1070 move, the pulse width and the period (or frequency) of the user-supplied waveform 1020A/1020B change as well.

The time period corresponding to the pulse width (distance between the starting point 1050 and the pulse width marker 1060) is referred to as a stimulation period or stimulation phase. The time period corresponding to the distance from the pulse width marker 1060 to the period marker 1070 may be referred to as an idle time period before the stimulation waveform should be repeated. This idle time period may also be used to implement a recovery phase. One purpose of the recovery phase is for charge-balancing—to get an integral of the stimulation current over the time periods of the stimulation phase and the recovery phase to zero. If the stimulation phase is not accompanied by a recovery phase, the integral of the current (which is the amount of charge) would be non-zero. This non-zero charge would damage the body tissue of the patient receiving the stimulation therapy. The recovery phase ensures that no such net charge will be built up. In other words, the recovery phase is implemented to prevent tissue damage. In some embodiments, the recovery phase may be configured such that its amplitude or its duration may be specified by a user, as long as the total area "under" (or "over") it is equal to the total area "over" (or "under") the stimulus curve. In other words, the amplitude and the duration of the recovery phase are inversely correlated, and once one of them is specified, the other one is automatically calculated to ensure that the "area under the curve" for the recovery phase is equal to the "area over the curve" for the stimulation phase.

The stimulation phase and the recovery phase are parts of a stimulation cycle, which repeats itself until the stimulation therapy is turned off. The patient is technically not being electrically stimulated during the recovery phase. However, at the typical stimulation frequency range (e.g., from 15 Hz to 300 Hz), the stimulation feels continuous to the patient. The patient cannot distinguish the stimulation and recovery phases based on his feelings, and thus the patient does not feel any interruptions in the stimulation.

Figure 15:
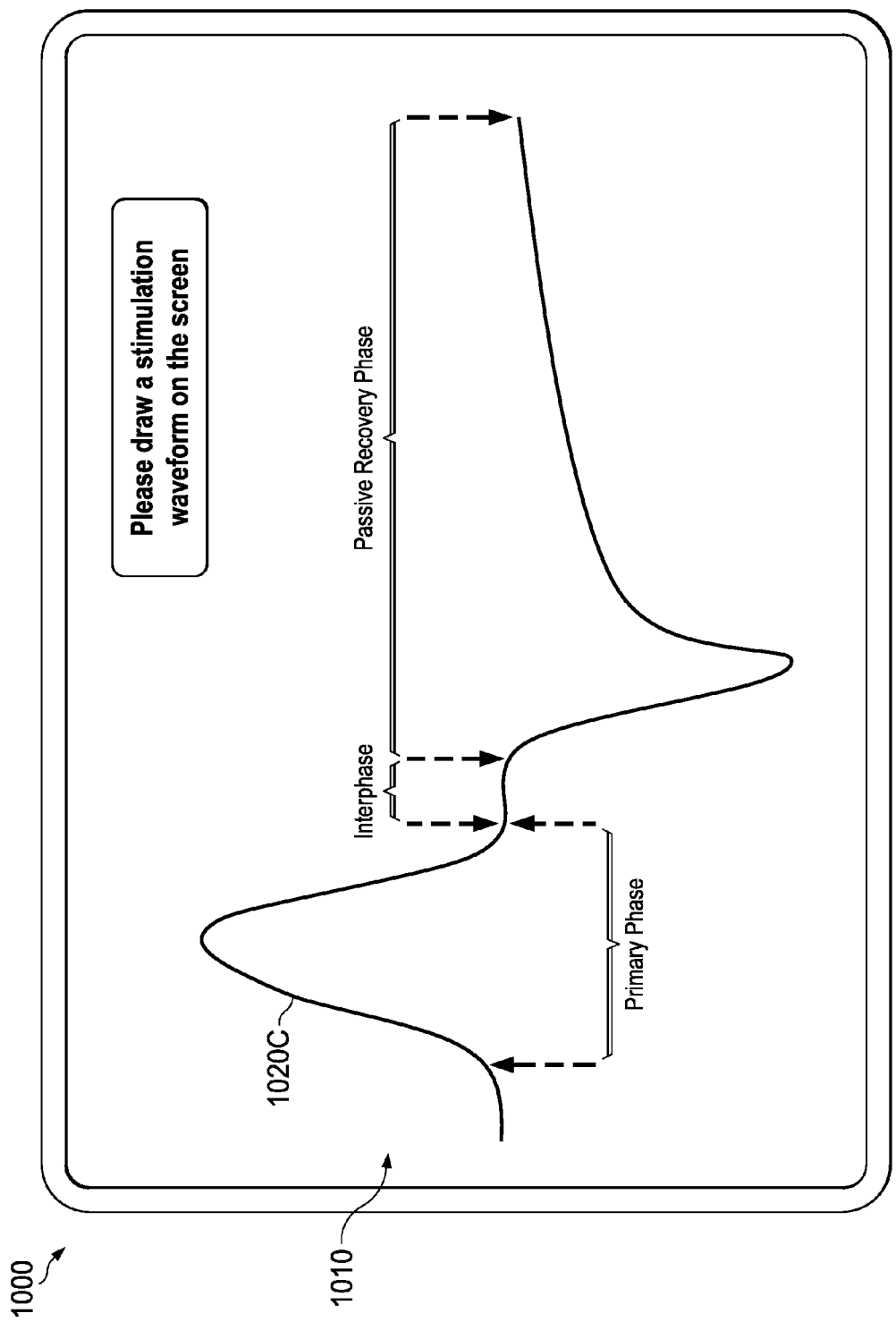
Figure 16:
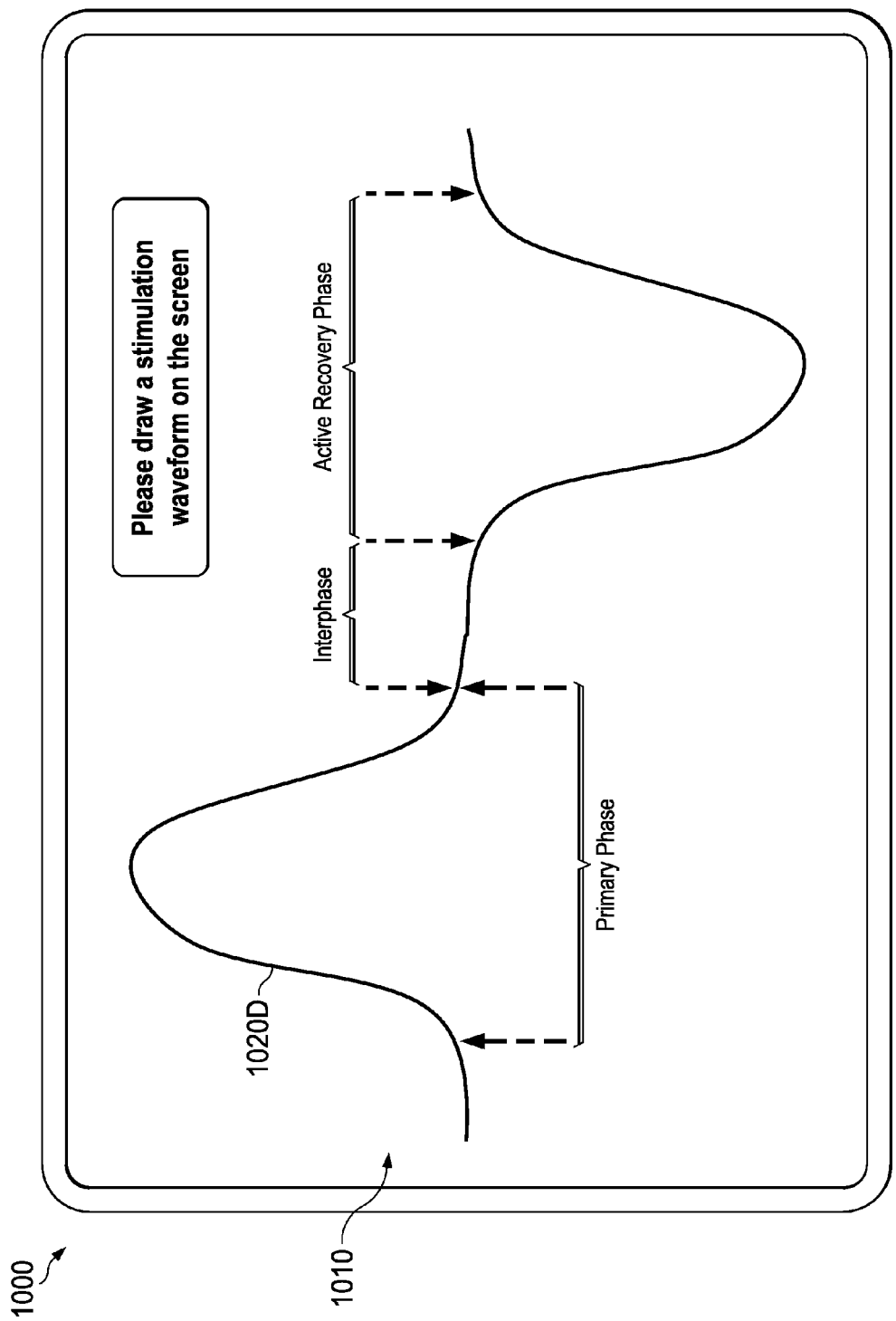

The recovery phase generally lasts longer than the stimulation phase. For example, the recovery phase may be between about 2-10 times longer than the stimulation phase. In some embodiments, the recovery phase may last for about 400 microseconds to about 10 milliseconds (compared to about 100 microseconds to about 150 microseconds for the stimulation phase). The recovery phase may also be passive or active. To illustrate, a hand-drawn waveform 1020C with a passive recovery phase is shown in FIG. 15, and a hand-drawn waveform 1020D with an active recovery phase is shown in FIG. 16.

The waveform 1020C and the waveform 1020D each include a primary phase (i.e., the stimulation phase), a recovery phase, and an interphase period between the primary phase and the recovery phase. For the waveform 1020C, the charges are passively rebalanced over time. In comparison, for the waveform 1020D, a "pulse" that is opposite in polarity (but substantially equal in amplitude) of the actual pulse (e.g., generated in the primary phase) is generated to allow the charges to balance more quickly. Therefore, the trade-off between passive recovery and active recovery is that passive recovery consumes less power but takes longer, and active recovery consumes more power but is quicker, which allows for stimulation at a higher frequency. Of course, it is understood that the active recovery may be configured differently. For example, rather than providing an active recovery phase that is the same in pulse width and amplitude (but having opposite polarity) as the primary phase, the active recovery phase may be configured to have an amplitude that is half of the amplitude of the primary phase (still opposite in polarity) and a pulse width that is twice as long as the primary phase.

In some embodiments, the user need not specifically draw the active or passive recovery phase. Rather, the user only needs to draw the active stimulation phase (the primary phase), and the electronic programmer 1000 may be configured to automatically generate an active recovery or a passive recovery phase to charge balance the stimulation phase. In some embodiments, the user may reserve a time period for the recovery phase by setting the markers 1060 and 1070, such as in FIGS. 13 and 14. In other embodiments, the user may draw both the stimulation phase and the recovery phase. The electronic programmer may then determine whether the user has drawn the correct charge balancing curve (including both the stimulation phase and the recovery phase) by computing the total area under the curve to see if the sum is equal to zero $\int_{Start}^{Period} W(t)=0$.

In either case, the electronic programmer 1000 will automatically generate a portion of a waveform corresponding to the recovery phase that cancels out the charge accumulated in the primary phase. The user may be given a choice to specify whether a passive recovery or an active recovery is desired, and the user may even be allowed to customize the parameters of the active recovery (e.g., amplitude or pulse width of the recovery phase). It is also understood that in some embodiments, the user may be allowed to choose to skip the charge balancing confirmation, so that the stimulation will be performed using the unmodified waveform (i.e., the waveform that is not charge-balanced).

The electronic programmer 1000 employs at least two different methods of assigning specific units values (e.g., the number of milli-amps for stimulation current amplitude, or the number of microseconds for stimulation pulse width) to the user-supplied stimulation waveform. In one embodiment, the user-supplied stimulation waveform is initially unit-less. The stimulation waveform is digitized into a plurality of unit-less numbers, for example X-axis (horizontal) coordinates and Y-axis (vertical) coordinates. These numbers are then loaded into the memory 310 of the electronic programmer 1000. The user programs the stimulation parameters in a later process, for example in a manner described in U.S. patent application Ser. No. 13/601,631, filed on Aug. 31, 2012 and entitled "Programming and Virtual Reality Representation of Stimulation Parameter Groups", the disclosure of which is herein incorporated by reference in its entirety. When the user specifies the values of the stimulation parameters as a part of the stimulation programming, the unit-less numbers are then assigned the units based on the values of the programmed stimulation parameters. For example, the user may specify that the value of a maximum stimulation amplitude is 2 mA. According, the Y-axis value corresponding to the peak of the user-supplied waveform is assigned to be 2 mA, and the rest of the quantized numbers are each assigned an appropriate stimulation current amplitude value proportionally.

In another embodiment, the user interface 1010 may display X-axes and Y-axes with scales and units (or grids), similar to an oscilloscope. An example of this approach is illustrated in FIG. 14. For example, each grid may correspond to an X number of microseconds and a Y number of milli-amps. In this manner, as the user draws the waveform 1020B on the graphical user interface 1010, the user may determine approximately what the stimulation current amplitude or the pulse width/frequency are associated with the waveform 1020B.

Figure 17:
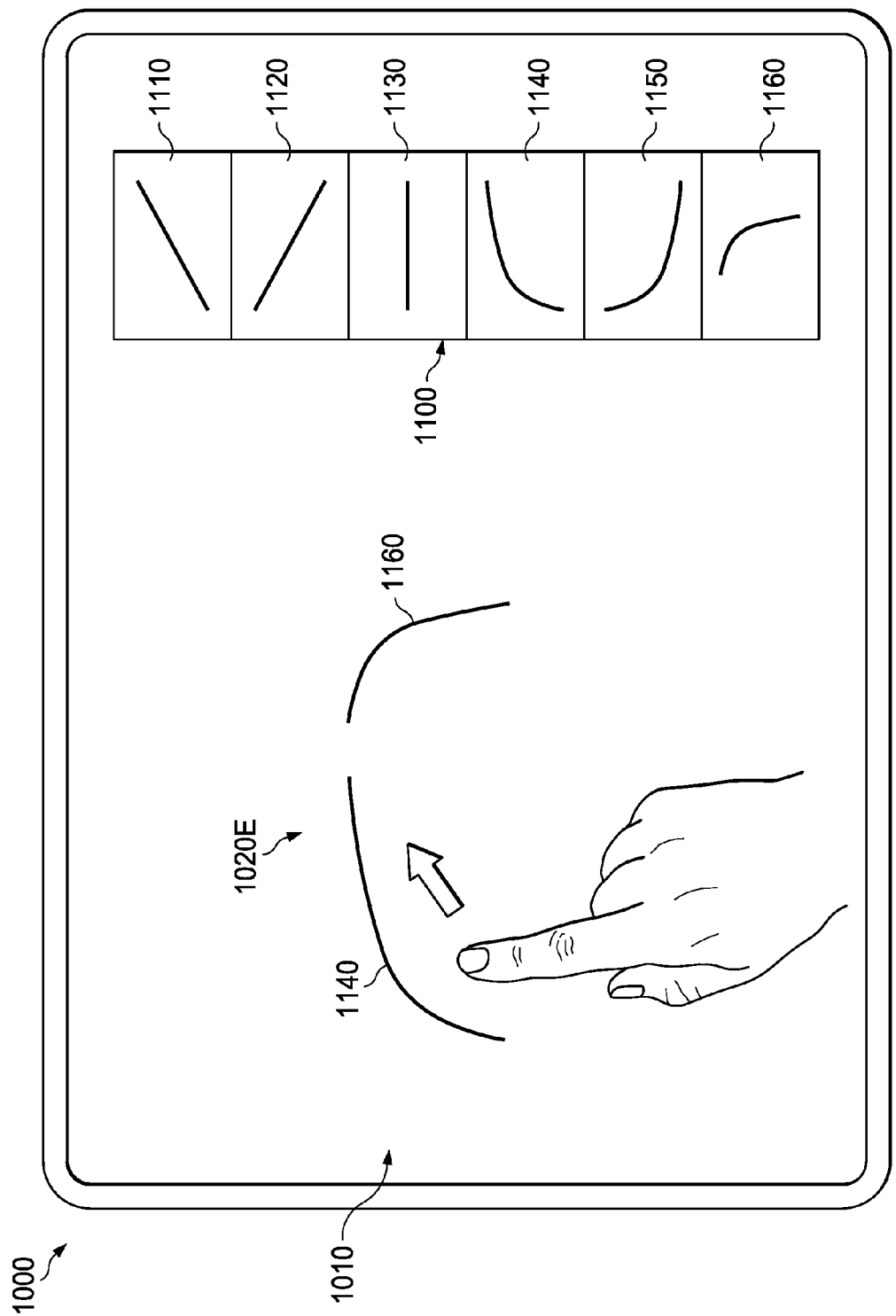

The examples discussed above with reference to FIGS. 13-16 pertain to the user using the graphical user interface 1010 to hand draw (by finger or by stylus) a stimulation waveform. FIG. 17 illustrates an alternative embodiment where the user may construct or piece together a stimulation waveform using a library that contains a plurality of pre-defined waveform segments. For example, the electronic programmer 1000 may include a library 1100 that is displayed via the graphical user interface 1010. The library 1100 contains a plurality of predefined waveform segments, some examples of which are illustrated in FIG. 17 as waveform segments 1110-1160. These waveform segments 1110-1160 may be selected (for example by touching/pressing with the user's finger or stylus) by the user and then manipulated (for example by moving, resizing, and/or rotating with the user's finger(s) or stylus) by the user so as to construct a user-defined or user-supplied stimulation waveform. In the example shown, the user selects the waveform segments 1140 and 1160 and is in the process of piecing them together to construct a part of a stimulation waveform 1120E.

It is understood that the library 1100 illustrated in FIG. 17 only shows a small sample of available predefined waveform segments. These waveform segments may also be defined (for example by drawing them) by the user (or other users) and then uploaded to a centralized database, for example the database 900 of FIG. 12. The waveform segments may also be downloaded to the electronic programmer 1000 from the centralized database 900. In this manner, the number of available waveform segments may expand continuously. It is also understood that the library 1100 may be used to construct not just the stimulation phase, but also the recovery phase, of the stimulation waveform. Alternatively, separate libraries may be used to construct the stimulation phase and the recovery phase of the waveform.

Figure 18:
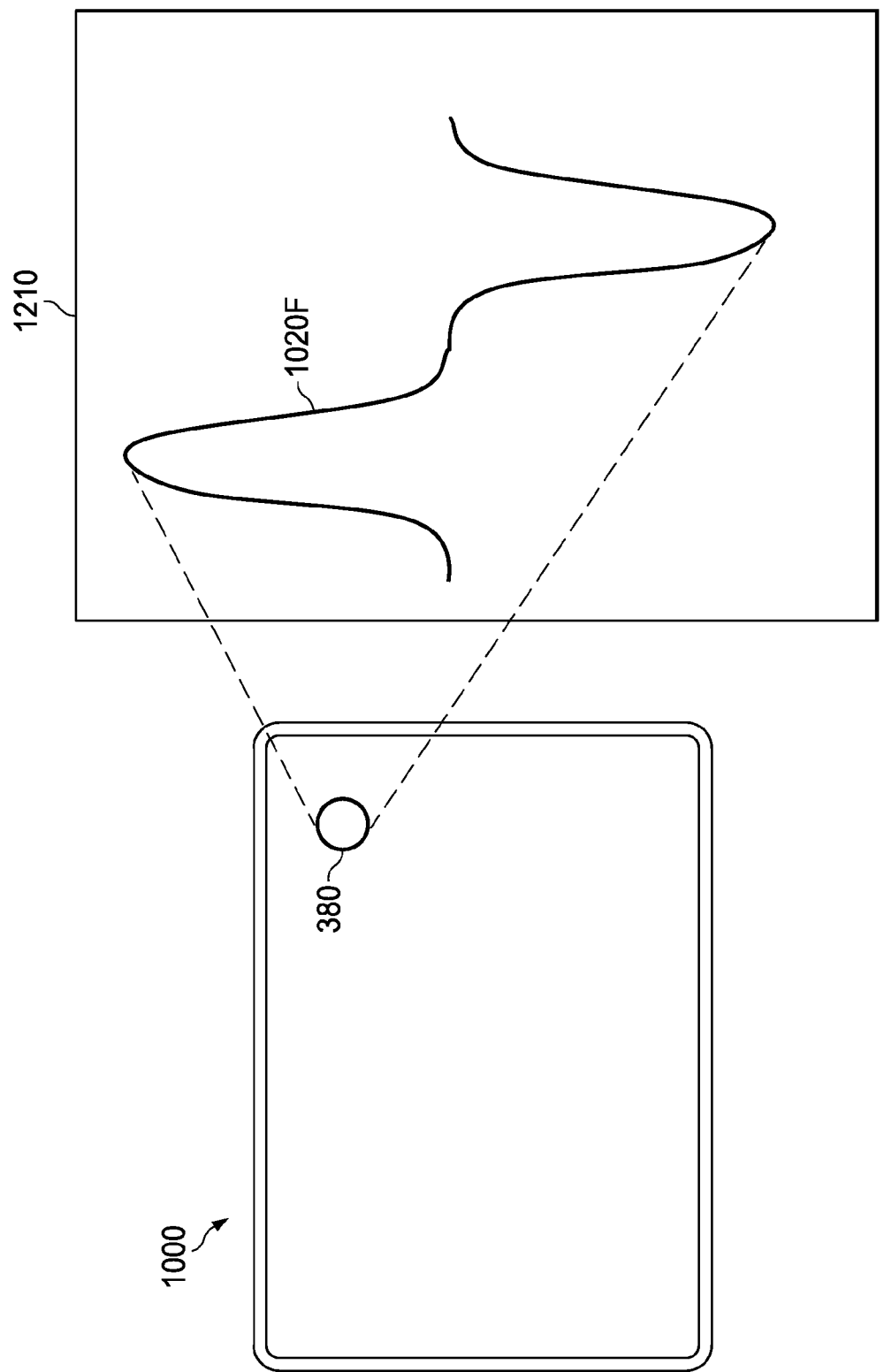
FIG. 18 illustrates a system of optically scanning a waveform sketched on a tangible medium according to various aspects of the present disclosure.

FIG. 18 illustrates another embodiment of providing a user-supplied waveform. The user may obtain a sketch of a stimulation waveform 1020F that is displayed on a tangible medium 1210. In some embodiments, the tangible medium 1210 is a piece of paper. In other words, the user or someone else has drawn the waveform sketch 1020F on that piece of paper. The waveform drawn on paper may also be from a printed publication, such as a text book, a magazine, an article, or scholarly paper. In other embodiments, the tangible medium 1210 is a computerized display. For example, the waveform sketch 1020F may be displayed on a television set, a desktop computer, a laptop computer, a tablet computer, or even a mobile telephone.

The waveform sketch 1020F may be electronically captured by an optical imaging scan. In the embodiment illustrated in FIG. 18, the waveform sketch 1020F is captured by the camera 380 (discussed above with reference to FIG. 7) of the electronic programmer 1000. The electronic programmer 1000 contains image processing and/or pattern recognition software (e.g., stored on the memory 310 discussed above with reference to FIG. 7), which can be executed by the processor 300 (also discussed above with reference to FIG. 7) to translate the waveform 1020F captured by the camera 380 into a data format that is known by the electronic programmer 1000. In other embodiments, the optical imaging scan may also be performed by a standalone camera, or an electronic device with optical imaging capabilities (e.g., a smartphone such as the APPLE® IPHONE® or a tablet computer such as the APPLE® IPAD®). Once captured, the image containing the waveform 1020F may be electronically transferred to the electronic programmer 1000 via one or more suitable telecommunications links. The waveform is then processed by the electronic programmer 1000 to obtain data in a format known by the electronic programmer 1000.

In yet other embodiments, arbitrary waveforms may be downloaded from a centralized database where health care professionals can approve and upload known therapeutically safe waveforms. For example, the electronic programmer 1000 is telecommunicatively coupled to the database 900 (also interchangeably referred to as a "cloud" or "cloud server") discussed above with reference to FIG. 12. Stimulation waveforms can be archived in the database 900 based on therapy or for research purposes. The stimulation waveforms can be made available to download to users with an approved electronic programmer, or restrictions can be imposed on the access of this database 900. For example, if the waveforms are intended to be for research only, users outside of the research consortium may not have access. The user of the electronic programmer 1000 (and other similar users) can upload their own user-supplied stimulation waveform to the database 900 to be evaluated by other peers in the field. Once approved, these user-supplied stimulation waveforms can be downloaded by other approved electronic programmers as well.

Regardless of the specific method of inputting the user-supplied waveform into the electronic programmer 1000, once the waveform is entered into the electronic programmer, the electronic programmer may apply a set of pre-defined rules or restrictions to the waveform to determine the user-supplied waveform is compliant with these rules or restrictions. In some embodiments, the predefined rules or restrictions are based on the stimulation therapy settings. For example, the therapy settings may specify that the frequency of the stimulation waveform should be between 50 Hz and 200 Hz, and/or that the pulse width of the stimulation waveform should be between 220 microseconds and 440 microseconds. In some other embodiments, the predefined rules or restrictions are based on mathematical limitations. For example, for a waveform that employs a stimulus phase that is equal to the recovery phase, the frequency has to be $$\frac{1}{2*PulseWidth}.$$

In a more realistic situation, other time delays also have to be considered, such as software or hardware initialization or un-initialization times, which leads to a frequency that is equal to $$\frac{1}{2*PulseWidth+\Delta}.$$

In other embodiments, the predefined rules or restrictions are dictated by the limitations of the pulse generator that will eventually generate the pulses based on the user-supplied stimulation waveform. In yet other embodiments, the rules or restrictions may include charge correction, charge balance, charge density, etc. For example, charge per phase is the area under the waveform. Given the waveform inputted into the electronic programmer 1000 by the user, the electronic programmer can calculate the amount of charge per phase. Also given the number of electrode contacts that are in use, charge density can be calculated as charge divided by the number of electrode contacts. The calculated charge density has to be within a predefined acceptable limit.

Regardless of how the rules and restrictions are specified, the electronic programmer 1000 checks the characteristics or parameters of the user-supplied waveform (e.g., waveforms 1020A-1020F discussed above) to determine whether they are within the predefined ranges. For example, the frequency and/or the pulse width of the user-supplied waveform may be determined by performing calculations based on the starting point 1050, the pulse width marker 1060, and the period marker 1070 discussed above with reference to FIGS. 13-14.

In the example where the waveform frequency is specified to be within 50-200 Hz and the waveform pulse width is specified to be within 220-440 microseconds, if any of the waveforms 1020A-1020F has a frequency that is less than 50 Hz or greater than 200 Hz, or if any of the waveforms 1020A-1020F has a pulse width that is less than 220 microseconds or greater than 440 microseconds, then the electronic programmer 1000 will determine that the waveform is not compliant with the predefined rules or restrictions.

Figure 19:
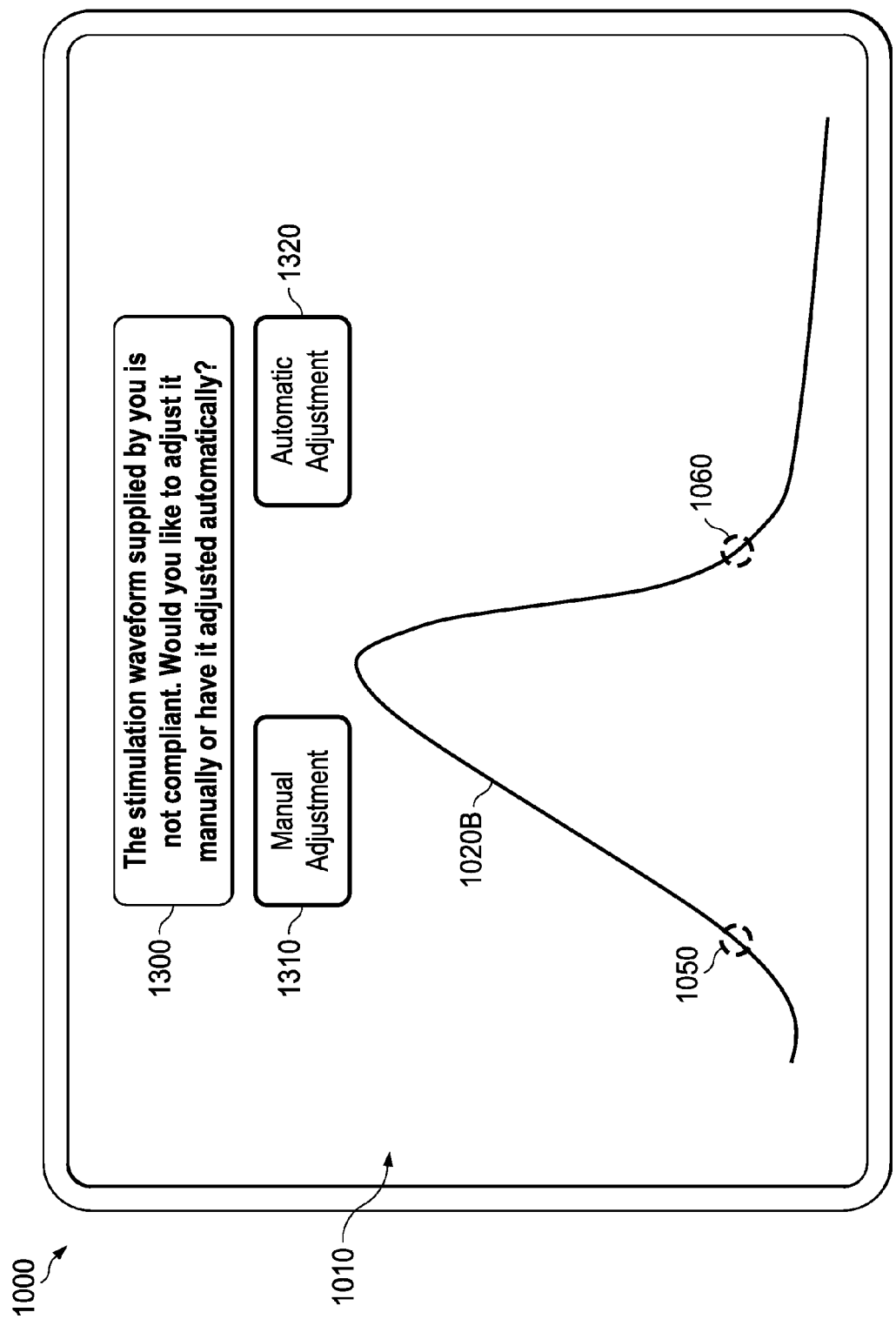

Upon detecting a non-compliant waveform, the electronic programmer 1000 may notify the user of the non-compliance. For example, referring to FIG. 19, the graphical user interface 1010 of the electronic programmer 1000 may display a message 1300 "The stimulation waveform supplied by you is not compliant. Would you like to adjust it manually or automatically?" or something similar. In various embodiments, the message 1300 may also include details regarding what parameter of the waveform is causing the compliance violation. For example, the message 1300 may state that the pulse width is too high, or the frequency is too low, etc.

The graphical user interface 1010 of the electronic programmer 1000 may also display clickable virtual buttons 1310 and 1320 to ask whether the user wants to manually correct the waveform or have the waveform automatically corrected until it is compliant with the predefined rules or restrictions. In the embodiment shown in FIG. 19, suppose that the pulse width of the waveform 1020B is too high (e.g., greater than 440 microseconds). The user may click on the button 1310, which then allows the user to manually adjust the waveform 1020B, such as pinching the waveform 1020B to "shrink" it horizontally, or by changing the locations of the starting point 1050 or the pulse width marker 1060.

In some embodiments, as the user is performing the manual adjustment of the waveform 1020B, the electronic programmer 1000 may communicate a notification to the user via a suitable feedback mechanism to let the user know that that the adjusted waveform is now compliant. The feedback mechanism may include playing an audible tone (e.g., a chime), or displaying a visual cue (e.g., an LED flash or changing the color of the waveform 1020B or the background thereof), or causing a tactile sensation (e.g., vibrating the electronic programmer 1000), etc. In other words, the electronic programmer 1000 may continuously calculate the new pulse width as the waveform 1020B is being adjusted/updated by the user. Once the electronic programmer 1000 detects that the new pulse width is within the acceptable range, it will send the feedback signal.

The user may also click on the button 1320, which then triggers an automatic adjustment of the waveform 1020B by the electronic programmer 1000. In this example, since the excessively high pulse width (greater than 440 microseconds) is causing the non-compliance, the electronic programmer automatically reshapes the waveform 1020B (e.g., by "shrinking" the waveform 1020B horizontally) such that the reshaped waveform has a pulse width that is less than or equal to 440 microseconds. In some embodiments, the user may also manually adjust the waveform after the automatic adjustment is completed, in order to further tweak the shape of the waveform.

Figure 20:
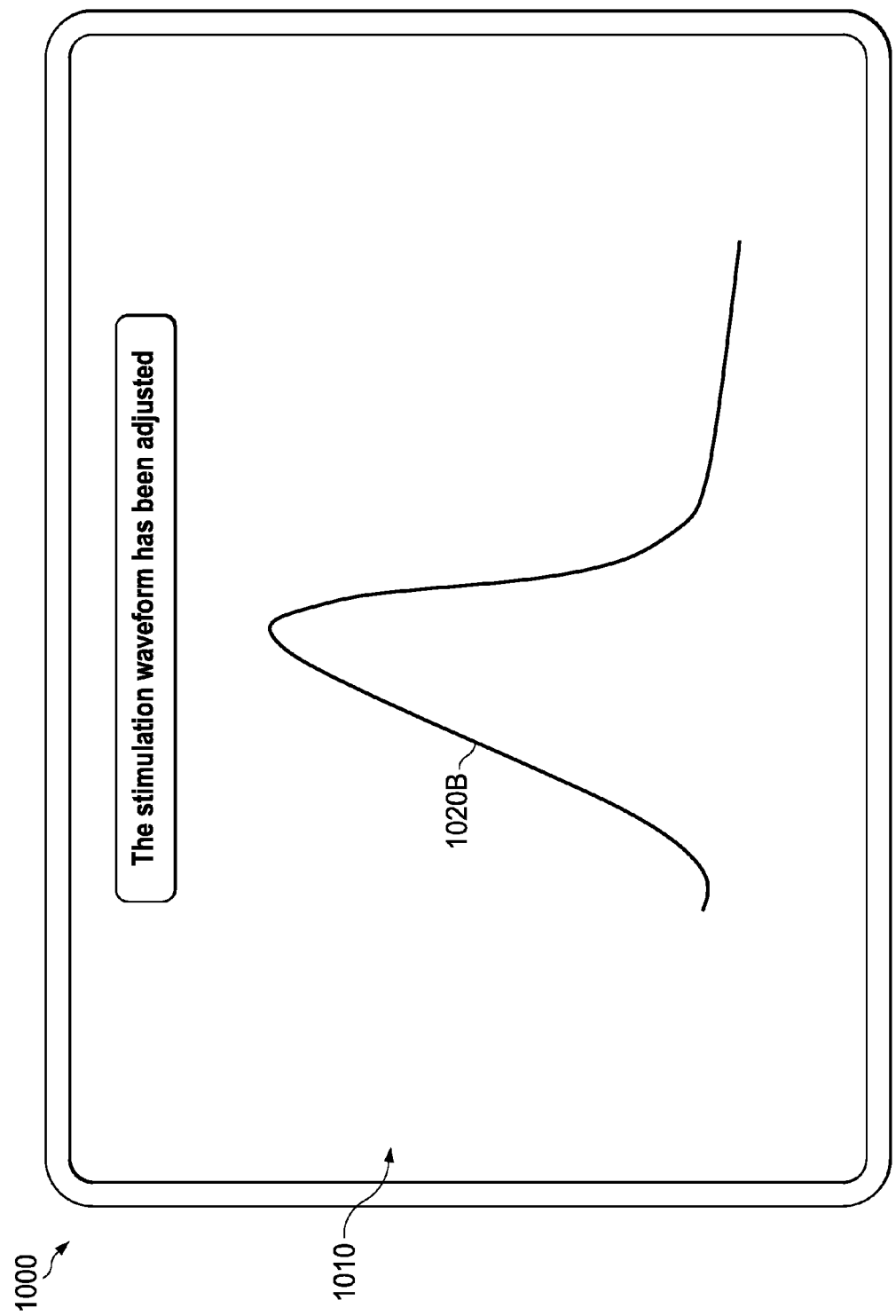

Regardless of whether the stimulation waveform is adjusted manually or automatically (or both), the electronic programmer 1000 may display the adjusted (and now compliant) waveform 1020B to the user, such as shown in FIG. 20. The electronic programmer 1010 may also display a message such as "The stimulation waveform has been adjusted" to the user.

Once the waveform passes the compliance test, and the user is satisfied with it, the electronic programmer 1000 may instruct the pulse generator 20 (discussed above with reference to FIGS. 2B and 8) to generate electrical stimulation pulses in accordance with the user-supplied waveform. The pulse generator 20 is configured to produce an arbitrarily-shaped stimulation waveform, as described in detail in U.S. Pat. No. 8,874,219, filed on Apr. 7, 2011, and issued on Oct. 28, 2014, the disclosure of which is hereby incorporated by reference in its entirety. The user may evaluate the efficacy of the electrical stimulation therapy provided by the user-supplied stimulation waveform by monitoring patient responses, such as bellows or toes responses described in U.S. patent application Ser. No. 14/537,293, filed on Nov. 12, 2014, and entitled "IPG CONFIGURED TO DELIVER DIFFERENT PULSE REGIMES TO DIFFERENT LEADS" to Kaula et. al., the disclosure of which is hereby incorporated by reference in its entirety. Based on the observed patient responses, the user may further modify the stimulation waveform and instruct the pulse generator to generate the modified stimulation waveform. The user may then monitor the user responses to determine whether the modified stimulation waveform led to an improvement in the therapy efficacy.

Alternatively, the user may determine the efficacy of the user-supplied stimulation waveform by asking the patient to provide feedback, for example via one of the patient feedback devices discussed above with reference to FIGS. 10A-10B and 11A-11C. Based on the patient feedback received, the user may further modify the stimulation waveform and instruct the pulse generator to generate the modified stimulation waveform.

Figure 21:
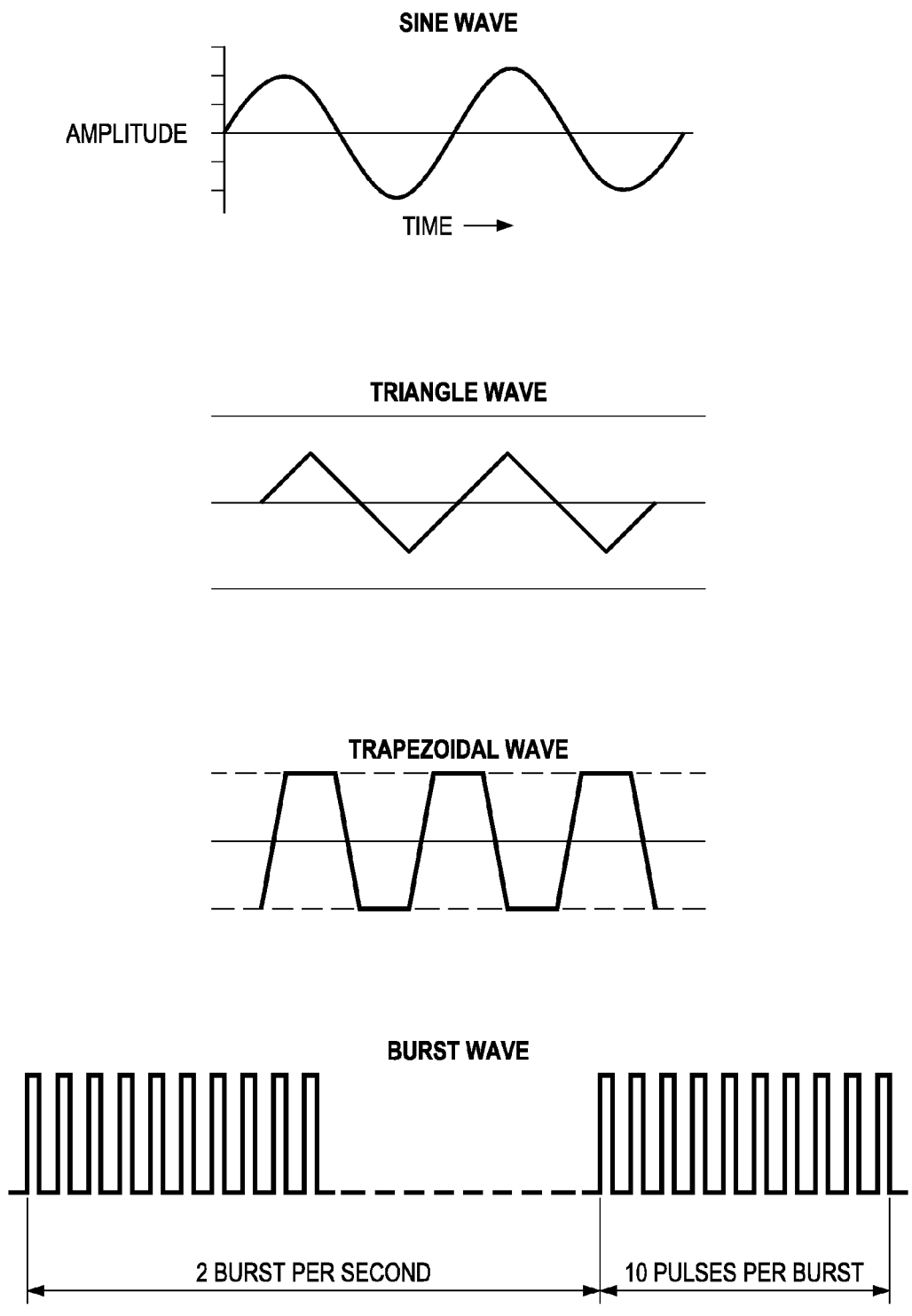
FIG. 21 illustrates various example predefined waveforms in a library according to various aspects of the present disclosure.

In addition to letting the user create or define a custom waveform having an arbitrary shape, the electronic programmer 1000 is also configured to provide a library of pre-approved stimulation waveforms. These waveforms may include, as examples, rectangular waveforms, triangular waveforms, trapezoidal waveforms, sinusoidal waveforms, seesaw-like waveforms, burst waveforms, or combinations thereof, etc. FIG. 21 illustrates some of these waveforms as examples. The user (e.g., healthcare professional) may select one of the waveforms from the library to apply for the stimulation therapy. In embodiments where the user prefers to draw a custom waveform, the electronic programmer 1000 may also try to match the waveform drawn by the user with one of the pre-approved waveforms in the library. The electronic programmer 1000 may then present this closest match to the user and ask him if that waveform can be used for stimulation instead. In some further embodiments, the electronic programmer 1000 may revise the pre-approved waveform that is the closest match with the one drawn by the user, so that it is an even better match while still passing all the predefined rules/restrictions discussed above.

It is understood that currently, patient programmers such as the patient programmer charger (PPC) and Pocket Programmer (PoP) discussed above with reference to FIGS. 3A-3B, 4, 5A-5B, and 6 populate programming settings according to the pulse generator (PG) they are paired with. Namely, they do not retain programming parameters if they are not paired with a PG. In one embodiment, the user such as a healthcare professional may download the different waveforms (e.g., user-supplied waveforms discussed above) directly to the patient devices. The patient can then download the waveforms as prescribed by the healthcare professional to the PG for different stimulation outcomes. In another embodiment, the PPC and PoP may be connected to the cloud (e.g., the database 900 in FIG. 12) so that waveforms approved by the healthcare professional can be made available to the patient programmers and further downloaded to the PG without the patient being physically present at a clinic. The patient programmers may be used to make finer adjustments to the waveforms via the cloud if feedback from the healthcare professional shows improvements by analyzing trends.

Figure 22:
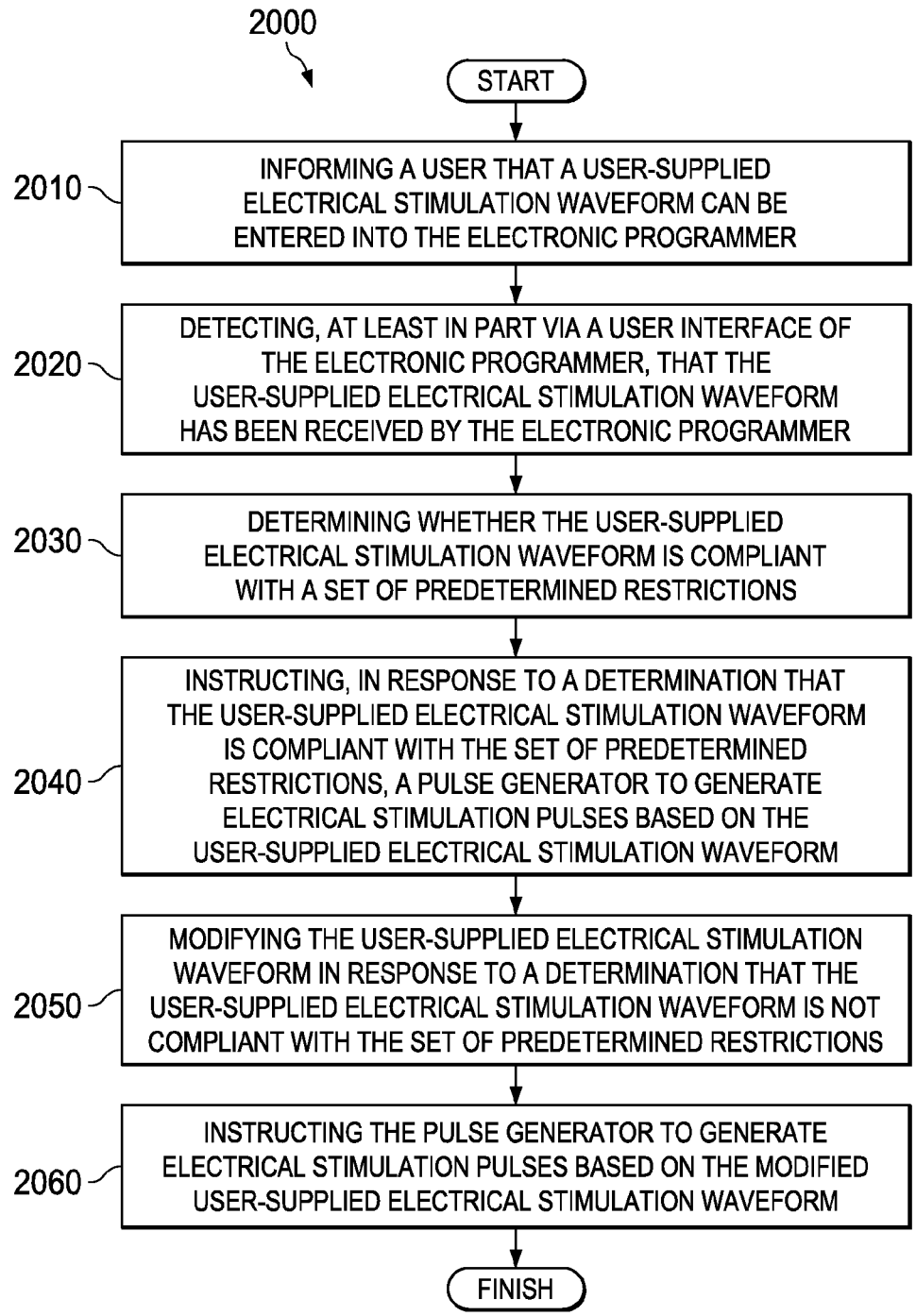
FIG. 22 is a flowchart illustrating a method of providing a stimulation therapy according to various aspects of the present disclosure.

FIG. 22 is a flowchart illustrating a method 2000 of providing an electrical stimulation therapy for a patient. In some embodiments, the steps of the method 2000 are performed by a portable electronic device, for example the clinician programmer discussed above with reference to FIGS. 2B and 7.

The method 2000 includes a step 2010 of informing a user that a user-supplied electrical stimulation waveform can be entered into an electronic programmer.

The method 2000 includes a step 2020 of detecting, at least in part via a user interface of the electronic programmer, that the user-supplied electrical stimulation waveform has been received by the electronic programmer. In some embodiments, the detecting comprises: detecting a waveform manually drawn on the user interface by a stylus or a finger of the user. In some other embodiments, the detecting comprises: capturing, via an optical imaging scan, a sketch of the waveform displayed on a tangible medium. In some embodiments, a library of different waveform segments is provided via the user interface. In these embodiments, the detecting comprises: receiving user selections of a subset of the waveform segments in the library, and constructing the user-supplied electrical stimulation waveform by piecing together the subset of waveform segments.

The method 2000 includes a step 2030 of determining whether the user-supplied electrical stimulation waveform is compliant with a set of predetermined restrictions.

The method 2000 includes a step 2040 of instructing, in response to a determination that the user-supplied electrical stimulation waveform is compliant with the set of predetermined restrictions, a pulse generator to generate electrical stimulation pulses based on the user-supplied electrical stimulation waveform.

The method 2000 includes a step 2050 of modifying the user-supplied electrical stimulation waveform in response to a determination that the user-supplied electrical stimulation waveform is not compliant with the set of predetermined restrictions. In some embodiments, the step 2050 of modifying comprises automatically changing a graphical characteristic of the user-supplied electrical waveform.

The method 2000 includes a step 2060 of instructing the pulse generator to generate electrical stimulation pulses based on the modified user-supplied electrical stimulation waveform.

It is understood that some of the steps 2010-2060 need not necessarily be performed sequentially unless otherwise specified. It is also understood that the method 2000 may include additional steps may be performed before, during, or after the steps 2010-2060. For example, the method 2000 may include a step of determining a pulse width or a frequency of the user-supplied electrical stimulation waveform via two or more markers placed on the waveform.

It is understood that at least some embodiments of the inventions discussed in the present disclosure are configurable for use in electrically stimulating the spinal cord, and other nerves, including the peripheral nerves, sacral nerves, and the brain. It is also understood that least some embodiments of the inventions discussed in the present disclosure are implemented via hardware (such as computer memories and CPUs, etc.) and software, for example using the clinician programmer discussed above with reference to FIG. 7 and/or the implantable pulse generator discussed above with reference to FIG. 8.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A electronic programmer, comprising:
   a user interface configured to receive an input from a user and communicate an output to the user;
   an electronic memory storage configured to store programming instructions; and
   one or more processors configured to execute the programming instructions to perform the following steps:
      informing a user that a user-supplied electrical stimulation waveform can be entered into the electronic programmer, wherein the user-supplied electrical stimulation waveform includes a stimulation phase and a recovery phase;
      detecting, at least in part via the user interface of the electronic programmer, that the user-supplied electrical stimulation waveform has been received by the electronic programmer;
      determining whether the user-supplied electrical stimulation waveform is compliant with a charge balancing so that an amount of charge for the recovery phase cancels out an amount of charge for the stimulation phase; and
      instructing, in response to a determination that the user-supplied electrical stimulation waveform is compliant with the charge balancing, a pulse generator to generate electrical stimulation pulses based on the user-supplied electrical stimulation waveform.

2. The electronic programmer of claim 1, wherein the steps further comprise:
   modifying the user-supplied electrical stimulation waveform in response to a determination that the user-supplied electrical stimulation waveform is not compliant with the charge balancing; and
   instructing the pulse generator to generate electrical stimulation pulses based on the modified user-supplied electrical stimulation waveform.

3. The electronic programmer of claim 2, wherein the modifying comprises automatically changing a graphical characteristic of the user-supplied electrical waveform.

4. The electronic programmer of claim 1, wherein the detecting comprises: detecting a waveform manually drawn on the user interface by a stylus or a finger of the user.

5. The electronic programmer of claim 1, wherein the detecting comprises: capturing, via an optical imaging scan, a sketch of the waveform displayed on a tangible medium.

6. The electronic programmer of claim 1, wherein the steps further comprise: displaying, via the user interface, a library of different waveform segments;
   wherein the detecting comprises:
   receiving user selections of a subset of the waveform segments in the library; and
   constructing the user-supplied electrical stimulation waveform by piecing together the subset of waveform segments.

7. The electronic programmer of claim 1, wherein the steps further comprise: determining a pulse width or a frequency of the user-supplied electrical stimulation waveform via two or more markers placed on the waveform.

8. A medical system, comprising:
   a pulse generator configured to generate electrical stimulation pulses as a part of an electrical stimulation therapy for a patient;
   an electronic programmer that is telecommunicatively coupled to the pulse generator through a communications link, wherein the electronic programmer is configured to perform the following steps:
      informing a user that a user-supplied electrical stimulation waveform can be entered into the electronic programmer, wherein the user-supplied electrical stimulation waveform includes a stimulation phase and a recovery phase;
      detecting, at least in part via a user interface of the electronic programmer, that the user-supplied electrical stimulation waveform has been received by the electronic programmer;
      determining whether the user-supplied electrical stimulation waveform is compliant with a charge balancing so that an amount of charge for the recovery phase cancels out an amount of charge for the stimulation phase; and
      instructing, in response to a determination that the user-supplied electrical stimulation waveform is compliant with the charge balancing, the pulse generator to generate electrical stimulation pulses based on the user-supplied electrical stimulation waveform.

9. The medical system of claim 8, wherein the steps further comprise:
   modifying the user-supplied electrical stimulation waveform in response to a determination that the user-supplied electrical stimulation waveform is not compliant with the charge balancing; and
   instructing the pulse generator to generate electrical stimulation pulses based on the modified user-supplied electrical stimulation waveform.

10. The medical system of claim 9, wherein the modifying comprises automatically changing a graphical characteristic of the user-supplied electrical waveform.

11. The medical system of claim 8, wherein the detecting comprises: detecting a waveform manually drawn on the user interface by a stylus or a finger of the user.

12. The medical system of claim 8, wherein the detecting comprises: capturing, via an optical imaging scan, a sketch of the waveform displayed on a tangible medium.

13. The medical system of claim 8, wherein the steps further comprise:
   displaying, via the user interface, a library of different waveform segments;
   wherein the detecting comprises:
   receiving user selections of a subset of the waveform segments in the library; and
   constructing the user-supplied electrical stimulation waveform by piecing together the subset of waveform segments.

14. The medical system of claim 8, wherein the steps further comprise: determining a pulse width or a frequency of the user-supplied electrical stimulation waveform via two or more markers placed on the waveform.

15. A method of providing electrical stimulation therapy for a patient, comprising:
informing a user that a user-supplied electrical stimulation waveform can be entered into an electronic programmer, wherein the user-supplied electrical stimulation waveform includes a stimulation phase and a recovery phase;
detecting, at least in part via a user interface of the electronic programmer, that the user-supplied electrical stimulation waveform has been received by the electronic programmer;
determining whether the user-supplied electrical stimulation waveform is compliant with a charge balancing so that an amount of charge for the recovery phase cancels out an amount of charge for the stimulation phase; and
instructing, in response to a determination that the user-supplied electrical stimulation waveform is compliant with the charge balancing, a pulse generator to generate electrical stimulation pulses based on the user-supplied electrical stimulation waveform.

16. The method of claim 15, further comprising:
modifying the user-supplied electrical stimulation waveform in response to a determination that the user-supplied electrical stimulation waveform is not compliant with the charge balancing; and
instructing the pulse generator to generate electrical stimulation pulses based on the modified user-supplied electrical stimulation waveform;
wherein the modifying comprises automatically changing a graphical characteristic of the user-supplied electrical waveform.

17. The method of claim 15, wherein the detecting comprises: detecting a waveform manually drawn on the user interface by a stylus or a finger of the user.

18. The method of claim 15, wherein the detecting comprises: capturing, via an optical imaging scan, a sketch of the waveform displayed on a tangible medium.

19. The method of claim 15, further comprising: displaying, via the user interface, a library of different waveform segments;
wherein the detecting comprises:
receiving user selections of a subset of the waveform segments in the library; and
constructing the user-supplied electrical stimulation waveform by piecing together the subset of waveform segments.

20. The method of claim 15, further comprising: determining a pulse width or a frequency of the user-supplied electrical stimulation waveform via two or more markers placed on the waveform.

* * * * *